United States Patent
Ishikawa et al.

(10) Patent No.: US 10,064,800 B2
(45) Date of Patent: Sep. 4, 2018

(54) TRANSGLUTAMINASE ACTIVATOR

(71) Applicant: Kao Corporation, Chuo-ku, Tokyo (JP)

(72) Inventors: Junko Ishikawa, Utsunomiya (JP); Shino Mitsunaga, Cambridge, MA (US); Shi Chen, Yokohama (JP); Akiko Kawasaki, Utsunomiya (JP); Yoshiya Sugai, Utsunomiya (JP); Yoshie Shimotoyodome, Shimotsuke (JP); Naoki Oya, Cincinnati, OH (US)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/424,648

(22) PCT Filed: Aug. 29, 2013

(86) PCT No.: PCT/JP2013/073208
§ 371 (c)(1),
(2) Date: Feb. 27, 2015

(87) PCT Pub. No.: WO2014/034802
PCT Pub. Date: Mar. 6, 2014

(65) Prior Publication Data
US 2015/0238404 A1    Aug. 27, 2015

(30) Foreign Application Priority Data

Aug. 29, 2012  (JP) ................................ 2012-188767
Aug. 29, 2012  (JP) ................................ 2012-188768
Dec. 20, 2012  (JP) ................................ 2012-278068

(51) Int. Cl.
| | |
|---|---|
| A61K 8/60 | (2006.01) |
| A61Q 19/00 | (2006.01) |
| A61K 8/97 | (2017.01) |
| A61K 36/19 | (2006.01) |
| A61Q 17/00 | (2006.01) |
| A61K 8/49 | (2006.01) |
| A61Q 5/04 | (2006.01) |
| C12N 9/10 | (2006.01) |
| A23L 33/105 | (2016.01) |

(52) U.S. Cl.
CPC ............ *A61K 8/602* (2013.01); *A23L 33/105* (2016.08); *A61K 8/4973* (2013.01); *A61K 8/97* (2013.01); *A61K 36/19* (2013.01); *A61Q 5/04* (2013.01); *A61Q 17/00* (2013.01); *A61Q 19/00* (2013.01); *C12N 9/1044* (2013.01)

(58) Field of Classification Search
CPC ......... A61K 36/19; A61K 8/97; A23L 33/105; A61Q 17/00; A61Q 19/00
See application file for complete search history.

(56) References Cited

U.S. PATENT DOCUMENTS

| | | |
|---|---|---|
| 2002/0150597 A1 | 10/2002 | Silva et al. |
| 2003/0124075 A1 | 7/2003 | Biatry et al. |
| 2004/0001792 A1 | 1/2004 | Biatry |
| 2008/0108681 A1 | 5/2008 | Scimeca et al. |
| 2009/0104295 A1 | 4/2009 | Kohno |
| 2011/0212041 A1 | 9/2011 | Tohi et al. |

(Continued)

FOREIGN PATENT DOCUMENTS

| | | |
|---|---|---|
| CN | 101732194 A | 6/2010 |
| CN | 102149366 A | 8/2011 |

(Continued)

OTHER PUBLICATIONS

Shyur, L-F. et al. "Antioxidant Properties of Extracts from Medicinal Plants Popularly Used in Taiwan" International Journal of Applied Science and Engineering 2005. 3, 3: 195-202.*

(Continued)

*Primary Examiner* — Andrew S Rosenthal
(74) *Attorney, Agent, or Firm* — Sterne, Kessler, Goldstein & Fox P.L.L.C.

(57) ABSTRACT

A transglutaminase activator containing at least one kind selected from the group consisting of an extract from *Justicia procumbens*, an extract from *Peristrophe japonica*, and a compound represented by Formula (1), as an active ingredient:

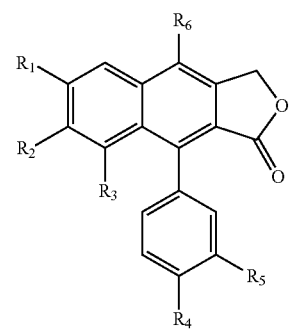

Formula (1)

wherein $R_1$ and $R_2$ represent a hydrogen atom, a hydroxyl group, or an alkoxy group having 1 to 4 carbon atoms; $R_3$ represents a hydrogen atom, or a group for forming a methylenedioxy group by bonding with $R_2$; $R_4$ and $R_5$ represent a hydrogen atom, or a group for forming a methylenedioxy group by bonding with each other; $R_6$ represents a hydrogen atom, a hydroxyl group, an alkoxy group having 1 to 5 carbon atoms, an acyloxy group having 1 to 4 carbon atoms, or a specific sugar residue.

22 Claims, No Drawings

(56) References Cited

U.S. PATENT DOCUMENTS

| | | |
|---|---|---|
| 2012/0329726 A1 | 12/2012 | Taguchi et al. |
| 2013/0295207 A1 | 11/2013 | Kikuchi et al. |
| 2014/0219940 A1 | 7/2014 | Kawasaki et al. |

FOREIGN PATENT DOCUMENTS

| | | | |
|---|---|---|---|
| DE | 100 59 107 A1 | 6/2001 | |
| EP | 1 181 927 A1 | 2/2002 | |
| JP | 1992-211609 A | 8/1992 | |
| JP | 05-186326 A | 7/1993 | |
| JP | 07-118135 A | 5/1995 | |
| JP | 09-151132 A | 6/1997 | |
| JP | 10-152421 A | 6/1998 | |
| JP | 2001-158735 A | 6/2001 | |
| JP | 2001-158736 A | 6/2001 | |
| JP | 2003-160429 A | 6/2003 | |
| JP | 2004-067676 A | 3/2004 | |
| JP | 2004-091376 A | 3/2004 | |
| JP | 2005-281206 A | 10/2005 | |
| JP | 2007-001914 A | 1/2007 | |
| JP | 2007-230977 A | 9/2007 | |
| JP | 2009-067701 A | 4/2009 | |
| JP | 2009-114146 A | 5/2009 | |
| JP | 2009-242310 A | 10/2009 | |
| JP | 2010-024190 A | 2/2010 | |
| JP | 2010-090093 A | 4/2010 | |
| JP | 2010-116371 A | 5/2010 | |
| JP | 2011-079755 A | 4/2011 | |
| WO | WO 2007/020755 A1 | 2/2007 | |
| WO | WO 2011/043330 A1 | 4/2011 | |
| WO | WO 2012/099247 A1 | 7/2012 | |
| WO | WO-2012099247 A1 * | 7/2012 | ........... A61K 31/365 |
| WO | WO 2012099247 A1 * | 7/2012 | ........... A61K 31/365 |
| WO | WO 2013/031403 A1 | 3/2013 | |

OTHER PUBLICATIONS

Kaur, K. et al. "Antimalarials from nature" Bioorg. Med. Chem. 2009, 17, 3229-3256.*

Machine translation of WO2012/099247 A1, accessed Apr. 11, 2016, pp. 1-22.*

Machine translation of WO2012/099247 A1, accessed Apr. 11, 2016, pp. 1-22. (Year: 2016).*

Mruthyunjayaswamy, B.H.M. et al. "Antiinflammatory Activity of Alcohol Extract of Justicia pr.ocumbens (Acanthaceae)" Indian Journal of Pharmaceutical Sciences, May-Jun. 1998, p. 173-175. (Year: 1998).*

Tofte, S.J. "Current management and therapy of atopic dermatitis" J Am Acad Dermatol 2001, S13-S16 (Year: 2001).*

John, S. et al. "Epidermal Transglutaminase (TGase 3) is Required for Proper Hair Development, but Not the Formation of the Epidermal Barrier" Plos One 2012, 7 (4), e34252, pp. 1-12. (Year: 2012).*

Chen, C-C. et al. "Antiplatelet Arylnaphthalide Lignans from Justicia procumbens" J. Nat. Prod. 1996, 59, 1149-1150 (Year: 1996).*

Hirobe, T. "Keratinocytes regulate the function of melanocytes" Dermatologica Sinica 32 (2014) 200-204 (Year: 2014).*

International Search Report (ISR) for PCT/JP2013/073208; I.A. fd: Aug. 29, 2013, dated Nov. 26, 2013, the Japanese Patent Office, Tokyo, Japan.

International Preliminary Report on Patentability (IPRP) including the Written Opinion of the International Searching Authority (PCT Rule 44bis) for PCT/JP2013/073208; I.A. fd: Aug. 29, 2013, dated Mar. 3, 2015, by the International Bureau of WIPO, Geneva, Switzerland.

Wang, C-C et al., "Constituents of Peritrophe japonica (Thunb.) Bremk," J. Chinese Chemical Society, 1992, 39(4): 351-353, Ke xue chu ban she, Peking, China.

Eghbali, N et al., "Silver-catalyzed one-pot synthesis of arylnaphthalene lactones," J. Org. Chem, Sep. 2008, 73:6932-6935, Am. Chem. Soc, Columbus, OH.

Kalinin, A et al., "Assembly of the epidermal cornified cell envelope," J. Cell Sci., Sep. 2001; 114: 3069-3070, Company of Biologists, Cambridge, England.

Rawlings, AV et al., "Stratum corneum moisturization at the molecular level: an update in relation to the dry skin cycle," J Invest Dermatol, Jun. 2005; 124(6): 1099-1110, Nature Publishing Group, New York, NY.

Ishikawa, J et al., "Dry skin in the winter is related to the ceramide profile in the stratum corneum and can be improved by treatment with a *Eucalyptus* extract," J. Cosmetic Dermatology, Mar. 2013, 21:3-11, Blackwell Science, Oxford, UK.

Modrak, DE et al., "Sphingolipid targets in cancer therapy," Mol. Cancer Ther., Feb. 2006; 5: 200-208, Am. Assoc. for Cancer Research, Inc., Philadelphia, PA.

Innocenti, G et al., "Patavine, a new arylnaphthalene lignan glycoside from shoot cultures of *Haplophyllum patavinum*," Chem Pharm Bull (Tokyo), Jun. 2002; 50(6): 844-846, Pharmaceutical Society of Japan, Tokyo, Japan.

Govindachari, TR et al., "Chemical constituents of *Cleistanthus collinus* (ROXB.)," Tetrahedron, 1969, 25: 2815-2821, Pergamon Press, Oxford, England.

Asano, J et al, "Antiviral activity of lignans and their glycosides from *Justicia procumbens*," Phytochemistry, Jun. 1996; 42(3): 713-717, Elsevier, London, England.

Lee, J-C et al, "Justicidin A decreases the level of cytosolic Ku70 leading to apoptosis in human colorectal cancer cells," Carcinogenesis, Oct. 2005; 26: 1716-1730, Irl Press at Oxford University Press, Oxford, England.

Kagan, VE et al., "Ascorbate is the primary reductant of the phenoxyl radical of etoposide in the presence of thiols both in cell homogenates and in model systems," Biochemistry, Aug. 1994; 33(32): 9651-9660, Am. Chem. Soc., Columbus, OH.

Parasuraman, S et al., "Computer-aided prediction of biological activity spectra, pharmacological and toxicological properties of cleistanthin A and B," Int. J. Res. Pharm. Sci, Jul.-Sep. 2010, 1(3): 333-337, JK Welfare & Pharmascope Foundtion, India.

Su, CL et al, "Caspase-8 acts as a key upstream executor of mitochondria during justicidin A-induced apoptosis in human hepatoma cells," FEBS Lett, May 2006; 580(13): 3185-3191, North-Holland on behalf of the Federation of European Biochemical Societies, Amsterdam, Netherlands.

Extended European search report including the supplementary European search report and the European search opinion, for EP Application No. 13831994.2, dated May 12, 2016, by the European Patent Office, Munich, Germany.

Okigawa, M. et al., "The isolation and structure of three new lignans from *Justicia procumbens* Linn. var. *leucantha* Honda," Tetrahedron 26:4301-4305 (1970), Pergamon Press.

Corrêa, GM et al., "Chemical constituents and biological activities of species of *Justicia*—a review," Revista Brasileira de Farmacognosia (Brazilian Journal of Pharmacognosy) 22(1): 220-238, Jan./Feb. 2012, Sociedade Brasileira de Farmacognosia. Elsevier Editora Ltda.

Pi, H-F et al., "Chemical constituents of *Peristrophe japonica*," Nat Prod Res Dev 20:269-270 (2008), Gai Kan Bianjibu, Chengdu, CN.

Liu, G et al., "Complete assignments of 1H and 13C NMR data for three new arylnaphthalene lignin from Justicia procumbens," Abstract only of article published at Magn. Reson. Chem. Mar. 2008; 46(3):283, Wiley Heyden, Chichester, England.

Nippon Shinyaku Co., Ltd., "Flower of This Month," Flower of Feb. 2008, Adhatoda [online], Hall of the herb, Pictorial book of flora DB, Feb. 2008, [searched on Feb. 22, 2017], author unknown, downloaded from the Internet www.nippon-shinyaku.co.jp/herb/db/flower/2008/justicia_adhatoda.html, printed Mar. 8, 2017.

Kamaraj, C et al., "Insecticidal and larvicidal activities of medicinal plant extracts against mosquitoes," Parasitol Res. Nov. 2010;107(6):1337-49. doi: 10.1007/s00436-010-2006-8. Epub Aug. 6, 2010, Springer International. Berlin, Germany.

Day, S-H et al., "Potent cytotoxic lignans from *Justicia procumbens* and their effects on nitric oxide and tumor necrosis factor-α production in mouse macrophages," J Nat Prod. Mar. 2002;65(3):379-381, DOI: 10.1021/np0101651; Epub Feb. 7, 2002, American Society of Pharmacognosy, Cincinnati, OH.

(56) References Cited

OTHER PUBLICATIONS

Guo, Y et al., "Role of mast cell histamine in the formation of rat paw edema: a microdialysis study," Eur J Pharmacol. Jul. 23, 1997;331(2-3):237-43, Elsevier Science, Netherlands.

Zhiling Wang et al., Calcium and Calcium Binding Protein versus Skin Differentiation and Damage Repair, ("gai he gai jie he dan bai yu pi fu fen hua he sun shang xiu fu."), Journal of Bethune Military Medical College, Apr. 30, 2009, vol. 7(2), pp. 97-99, Bethune Military Medical College, Shijiazhuang, China.

\* cited by examiner

TRANSGLUTAMINASE ACTIVATOR

TECHNICAL FIELD

The present invention relates to a transglutaminase activator, a ceramide production enhancer, and an involucrin expression enhancer.

BACKGROUND ART

The epidermal stratum corneum is responsible for providing a barrier function for preventing evaporation of moisture from the body and irritation or penetration by foreign matter from the exterior. The stratum corneum is constituted of corneocytes and intercellular lipids, and the corneocytes are enclosed within a cell membrane-like structure called the cornified envelope. The cornified envelope helps to establish a stable corneocyte structure and is an important structure for maintaining the skin barrier function. The cornified envelope is formed by cornification of keratinocytes in a basal layer of the horny cell layer and synthesis of involucrin (also referred to as "IVL" herein), loricrin other proteins necessary for cornification, whereafter the proteins are crosslinked by activation of transglutaminase. Expression and synthesis of the involucrin and activation of the transglutaminase are important for normal formation of the cornified envelope and normal epidermal cornification, and also for maintenance and improvement of the skin moisturizing function. In this respect, involucrin expression enhancement and transglutaminase activation are reported to lead to normal skin cornification, improvement of the barrier function and improvement of skin roughness (see, for example, Non-Patent Literatures 1 and 2, and Patent Literatures 1 and 2).

Moreover, ceramides, which are one class of sphingolipids, are lipids present only in an extremely small amount relative to the whole organism. However, in the stratum corneum which is the outermost layer of the skin, the content of ceramides is more than half that of lipids, and these ceramides play important roles in the moisturizing function and barrier function of the skin. These ceramides are produced in the epidermal cells, then secreted to form a lamellar structure in intercellular spaces of the stratum corneum, and they maintain the stratum corneum functions. It has been extensively reported that, in skin diseases such as dry skin, rough skin, atopic dermatitis, senile xerosis and psoriasis, normal metabolism of ceramides is inhibited and the amount of ceramides in the stratum corneum decreases, which leads to deterioration of moisturizing function, incomplete epidermal cornification, and decline in the barrier and other functions of the skin (see Non-Patent Literature 3). It is thought that a substance which enhances production of ceramides would have effects such as animal cell proliferation inhibition, differentiation induction, and apoptosis induction, and furthermore could be expected to have therapeutic effects on diseases due to cell proliferation or abnormal differentiation, such as inflammatory diseases and malignant tumors (see Non-Patent Literature 4). Moreover, it has been reported that ceramides have an effect of inhibiting bone resorption, an effect of strengthening bone, and an effect of inhibiting decrease in alveolar bone, and are useful for preventing and ameliorating bone and joint diseases such as osteoporosis, bone fracture, low back pain, and rheumatism (see Patent Literature 3), that ceramides have an effect of preventing or reducing periodontal diseases (see Patent Literature 4), and that ceramides have an effect of imparting bounce and resilience to the hair and an effect of improving the feel of the hair (see Patent Literature 5).

Thus, various efficacies can be expected from ceramides, and thus an effort to discover substances that can enhance ceramide production is desirable.

Moreover, cornification-related proteins such as involucrin are known to also play a role in hair growth. For example, it has been reported based on the result of gene expression analysis in the hair root that involucrin gene expression is significantly higher in persons with wavy hair, and that a substance that increases involucrin gene expression can act as a wavy hair or curly hair promoter or a wave formation enhancer (see Patent Literature 6).

On the other hand, the plants of family Acanthaceae contain about 250 genera and 2,500 species. Of these plants, those in the genus *Justicia* are believed to include about 300 species. Particularly noteworthy is that *Justicia procumbens* has been used as a Chinese medicine, for example, to treat arthritic pain and reduce fever, and that *Justicia gendarussa*, a plant in the same genus *Justicia*, is known as an ingredient of a skin analgesic for external application and a skin anti-itching agent for external application (see, for example, Patent Literatures 7 and 8). Moreover, *Adhatoda vasica*, a plant in a different genus in the same family Acanthaceae, is known to have a ceramide production enhancing effect (for example, Patent Literature 9). Further, physiological activities of an extract from *Justicia procumbens* are known to include a melanin formation inhibiting effect and a dopa oxidase activity inhibiting effect (for example, see Patent Literature 10).

However, the extract from *Justicia procumbens* has not up to now been known to activate transglutaminase and enhance ceramide production, or to be useful for maintaining or improving skin barrier function or moisturizing function, or preventing or improving skin roughness.

Moreover, an extract from *Peristrophe japonica*, a plant belonging to the family Acanthaceae, genus *Peristrophe*, is known to exhibit physiological activities including a melanin formation inhibiting effect, a dopa oxidase activity inhibiting effect, and the like (for example, see Patent Literature 11). However, the extract from *Peristrophe japonica* has not so far been known to activate transglutaminase and enhance ceramide production and involucrin expression, or to be useful for maintaining or improving skin barrier function or moisturizing function, or preventing or improving skin roughness, or forming wavy hair, curly hair, or wave formation.

Further, arylnaphthalene lignans are known to be isolatable from an extract from plants such as *Haplophyllum patavinum* and *Cleistanthus collinus* (see, for example, Non-Patent Literatures 5 and 6). Physiological activities of the arylnaphthalene lignans are known to include a bone resorption inhibiting effect, and a cell differentiation inducing factor reinforcing effect on osteoblasts and neurons (see, for example, Patent Literatures 12 and 13). Further, Justicidin A, Justicidin B, Diphyllin and Tuberculatin are known to have antiviral activity or antitumor activity (see, for example, Non-Patent Literatures 7 and 8). Furthermore, Justicidin A and Cleistanthin A are known to have antitumor activity (see, for example, Non-Patent Literatures 9 and 10, and Patent Literature 14), and a melanin formation inhibiting effect and a dopa oxidase activity inhibiting effect (for example, see Patent Literature 11), and the like. However, arylnaphthalene lignans represented by Formula (1) as set out below have not so far been known to activate transglutaminase and enhance the ceramide production and the involucrin expression, or to be useful for maintaining or improving the skin barrier function or moisturizing function, or preventing or improving skin roughness, and forming wavy hair or curly hair or wave formation.

CITATION LIST

Patent Literatures

Patent Literature 1: JP-A-2004-91376 ("JP-A" means unexamined published Japanese patent application)
Patent Literature 2: JP-A-2007-1914
Patent Literature 3: JP-A-2001-158736
Patent Literature 4: JP-A-2001-158735
Patent Literature 5: JP-A-10-152421
Patent Literature 6: WO 2011/043330
Patent Literature 7: JP-A-2005-281206
Patent Literature 8: JP-A-2007-230977
Patent Literature 9: JP-A-2011-79755
Patent Literature 10: WO 2013/031403
Patent Literature 11: WO 2012/099247
Patent Literature 12: JP-A-4-211609
Patent Literature 13: JP-A-9-151132
Patent Literature 14: Japanese patent No. 3099243

Non-Patent Literatures

Non-Patent Literature 1: Kalinin, A., et al., Journal of Cell Science, 2001, vol. 114, p. 3069-3070
Non-Patent Literature 2: Rawlings, A. V., et al., Journal of Investigative Dermatology, 2005, vol. 124, p. 1099-1110
Non-Patent Literature 3: Ishikawa, J., et al., Journal of Cosmetic Dermatology, 2013, vol. 12, p. 3-11
Non-Patent Literature 4: David E. Modrak, et al., Molecular Cancer Therapeutics, 2006, vol. 5(2), p. 200-208
Non-Patent Literature 5: G. INNOCENTI, et al., Chem. Pharm. Bull., 2002, vol. 50, p. 844-846
Non-Patent Literature 6: Govindachari, T. R., et al., Tetrahedron, 1969, vol. 25, p. 2815-2821
Non-Patent Literature 7: ASANO Jun, et al., Phytochemistry, 1996, vol. 42, p. 713-717
Non-Patent Literature 8: Jenq-Chang Lee, et al., Carcinogenesis, 2005, vol. 26, p. 1716-1730
Non-Patent Literature 9: Valerian E. Kagan, et al., Biochemistry, 1994, vol. 33, p. 9651-9660
Non-Patent Literature 10: Parasuraman S., et al., International Journal of Research in Pharmaceutical Sciences, 2010, vol. 1(3), p. 333-337

SUMMARY OF INVENTION

Problems that the Invention is to Solve

The present invention is contemplated for providing a new epidermal cornification improver, skin moisturizing function improver, skin barrier function improver, horny cell layer moisture content increasing agent, horny cell layer moisture content reduction inhibitor, skin roughness preventive or improver, and wavy hair former.

The present invention is also contemplated for providing a transglutaminase activator that activates transglutaminase, and is useful for maintaining or improving a skin barrier function or moisturizing function, or preventing or improving skin roughness.

The present invention is also contemplated for providing a ceramide production enhancer that enhances ceramide production, and is useful for maintaining or improving a skin barrier function or moisturizing function, or preventing or improving skin roughness.

The present invention is also contemplated for providing an involucrin expression enhancer that enhances involucrin expression, and is useful for maintaining or improving a skin barrier function or moisturizing function, or preventing or improving skin roughness, and forming wavy hair, frizzled hair, or wave formation.

Means to Solve the Problem

In view of the above-described problems, the present inventors diligently continued to conduct study. As a result, the present inventors found that an extract from *Justicia procumbens* activates the transglutaminase, enhances the ceramide production, increases a horny cell layer moisture content, inhibits horny cell layer moisture content reduction and prevents or improves skin roughness. Further, the present inventors found that an extract from *Peristrophe japonica* activates the transglutaminase, and enhances the ceramide production and the involucrin expression.

Further, the present inventors found that arylnaphthalene lignanes having specific structure activate the transglutaminase, and enhance the ceramide production and the involucrin expression.

The present invention was completed based on these findings.

The present invention relates to a transglutaminase activator containing an extract from *Justicia procumbens* as an active ingredient.

Further, the present invention relates to a ceramide production enhancer containing an extract from *Justicia procumbens* as an active ingredient.

Further, the present invention relates to an epidermal cornification improver containing an extract from *Justicia procumbens* as an active ingredient.

Further, the present invention relates to a skin moisturizing function improver containing an extract from *Justicia procumbens* as an active ingredient.

Further, the present invention relates to a skin barrier function improver containing an extract from *Justicia procumbens* as an active ingredient.

Further, the present invention relates to a horny cell layer moisture content increasing agent containing an extract from *Justicia procumbens* as an active ingredient.

Further, the present invention relates to a horny cell layer moisture content reduction inhibitor containing an extract from *Justicia procumbens* as an active ingredient.

Further, the present invention relates to a skin roughness preventive or improver containing an extract from *Justicia procumbens* as an active ingredient.

(Hereinafter, a first embodiment of the present invention means to include the transglutaminase activator, the ceramide production enhancer, the epidermal cornification improver, the skin moisturizing function improver, the skin barrier function improver, the horny cell layer moisture content increasing agent, the horny cell layer moisture content reduction inhibitor, and the skin roughness preventive or improver.)

The present invention relates to a transglutaminase activator containing an extract from *Peristrophe japonica* as an active ingredient.

Further, the present invention relates to a ceramide production enhancer containing an extract from *Peristrophe japonica* as an active ingredient.

Further, the present invention relates to an involucrin expression enhancer containing an extract from *Peristrophe japonica* as an active ingredient.

Further, the present invention relates to an epidermal cornification improver containing an extract from *Peristrophe japonica* as an active ingredient.

Further, the present invention relates to a skin moisturizing function improver containing an extract from *Peristrophe japonica* as an active ingredient.

Further, the present invention relates to a skin barrier function improver containing an extract from *Peristrophe japonica* as an active ingredient.

Further, the present invention relates to a skin roughness preventive or improver containing an extract from *Peristrophe japonica* as an active ingredient.

Further, the present invention relates to a wavy hair former containing an extract from *Peristrophe japonica* as an active ingredient.

(Hereinafter, a second embodiment of the present invention means to include the transglutaminase activator, the ceramide production enhancer, the involucrin expression enhancer, the epidermal cornification improver, the skin moisturizing function improver, the skin barrier function improver, the skin roughness preventive or improver, and the wavy hair former.)

The present invention relates to a transglutaminase activator containing at least one kind of compound represented by Formula (1) as an active ingredient.

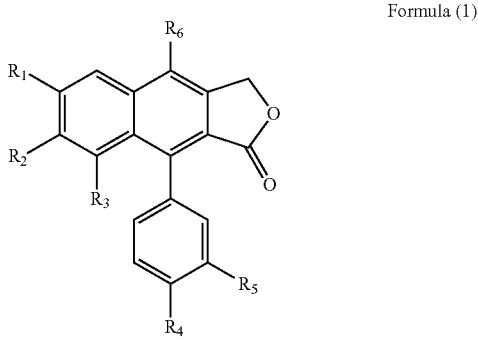

Formula (1)

[In Formula (1), $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (β-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid.]

Further, the present invention relates to a ceramide production enhancer containing at least one kind of compound represented by Formula (1) as an active ingredient.

Further, the present invention relates to an involucrin expression enhancer containing at least one kind of compound represented by Formula (1) as an active ingredient.

Further, the present invention relates to an epidermal cornification improver containing at least one kind of compound represented by Formula (1) as an active ingredient.

Further, the present invention relates to a skin moisturizing function improver containing at least one kind of compound represented by Formula (1) as an active ingredient.

Further, the present invention relates to a skin barrier function improver containing at least one kind of compound represented by Formula (1) as an active ingredient.

Further, the present invention relates to a skin roughness preventive or improver containing at least one kind of compound represented by Formula (1) as an active ingredient.

Further, the present invention relates to a wavy hair former containing at least one kind of compound represented by Formula (1) as an active ingredient.

(Hereinafter, a third embodiment of the present invention means to include the transglutaminase activator, the ceramide production enhancer, the involucrin expression enhancer, the epidermal cornification improver, the skin moisturizing function improver, the skin barrier function improver, the skin roughness preventive or improver, and the wavy hair former.)

Herein, the present invention means to include all of the above first, second and third embodiments, unless otherwise specified.

Effects of the Invention

The transglutaminase activator of the present invention activates transglutaminase, and is useful for maintaining or improving skin barrier function or skin moisturizing function or preventing or improving skin roughness.

The ceramide production enhancer of the present invention enhances ceramide production and is useful for maintaining or improving skin barrier function or skin moisturizing function or preventing or improving skin roughness, and the like.

The involucrin expression enhancer of the present invention enhances involucrin expression, and is useful for maintaining or improving skin barrier function, or preventing or improving skin roughness, and forming wavy hair, curly hair, and wave formation.

Other and further features and advantages of the invention will appear more fully from the following description.

MODE FOR CARRYING OUT THE INVENTION

In the present specification, "improve" as termed herein encompasses changing for the better of diseases, symptoms or conditions; preventing or delaying deterioration of diseases, symptoms or conditions; and reversal of progression, preventing progression and delaying progression of diseases, symptoms or conditions.

In addition, "non-therapeutic" as termed herein is a concept that does not encompass medical practices, namely, does not encompass treatments for human bodies for the purpose of treatment.

In addition, "prevent" as termed herein means that the developments of diseases or symptoms in individuals are prevented or delayed, or the risk of development of diseases or symptoms in individuals are lowered.

Further, "skin roughness" as termed herein means a state such as one in which skin moisturizing ability decreases and skin moisture is depleted, and desquamation or skin rhagades appear on the skin surface, or one in which skin surface roughness increases. Skin in such a state is also referred to as "rough skin" or "dry skin."

The transglutaminase activator, the ceramide production enhancer, the horny cell layer moisture content increasing agent and the horny cell layer moisture content reduction inhibitor of the first embodiment of the present invention contain an extract from *Justicia procumbens* as an active ingredient. As verified in Examples described later, the extract from *Justicia procumbens* has a transglutaminase activation effect, a ceramide production enhancing effect, a horny cell layer moisture content increasing effect and a horny cell layer moisture content reduction inhibiting effect.

Moreover, the epidermal cornification improver, the skin moisturizing function improver, the skin barrier function improver and the skin roughness preventive or improver of the first embodiment of the present invention also contain the extract from *Justicia procumbens* as an active ingredient. As mentioned above, the transglutaminase activation, the ceramide production enhancement, the horny cell layer moisture content increasing and the horny cell layer moisture content reduction inhibition are significantly important for improvement of epidermal cornification, improvement of skin moisturizing function, maintenance of skin barrier function, and prevention or improvement of skin roughness. Moreover, as verified in Examples described later, the extract from *Justicia procumbens* improves epidermal cornification, skin moisturizing function, and the skin barrier function, and prevents or improves skin roughness.

Accordingly, the extract from *Justicia procumbens* having the transglutaminase activation effect, the ceramide production enhancing effect, the horny cell layer moisture content increasing effect and the horny cell layer moisture content reduction inhibiting effect can be contained as the active ingredient in the epidermal cornification improver, the skin moisturizing function improver, the skin barrier function improver and the skin roughness preventive or improver.

Moreover, as mentioned above, ceramides play a role in control of cell proliferation, differentiation, apoptosis and the like. Therefore, the extract from *Justicia procumbens* that enhances the ceramide production is useful as a drug, a quasi drug or the like for preventing or treating diseases caused by abnormality of cell proliferation or differentiation, such as inflammatory diseases and malignant tumors, by animal cell proliferation inhibition, differentiation induction, apoptosis induction, and the like. Moreover, the extract from *Justicia procumbens* can also be used for a drug, a quasi drug or the like for preventing or improving bone and joint diseases such as osteoporosis, bone fracture, lumbago and rheumatoid arthritis, or for preventing or improving periodontosis. Further, the extract from *Justicia procumbens* is also useful as a quasi drug, a cosmetic or the like for providing hair with bounce and resilience or improving the feel of the hair.

In the present specification, "*Justicia procumbens*" is an annual plant which belongs to the family Acanthaceae, genus *Justicia*.

In manufacture of the extract from *Justicia procumbens*, an arbitrary part of *Justicia procumbens* can be used; and an entire plant, a root, a tuberous root, a rhizome, a stock, a branch, a stem, a leaf (a leaf blade, a petiole or the like), a bark, a sap, a resin, a flower (a petal, an ovary or the like), a fruit (a ripe fruit, an unripe fruit or the like), a seed or the like can be used therefor. A plurality of these parts may be used in combination thereof. Above all, the extract from *Justicia procumbens* to be used in the first embodiment of the present invention is preferably an extract from the entire plant of *Justicia procumbens*.

The transglutaminase activator, the ceramide production enhancer, and the involucrin expression enhancer of the second embodiment of the present invention contain an extract from *Peristrophe japonica* as an active ingredient. As verified in Examples described later, the extract from *Peristrophe japonica* has a transglutaminase activation effect, a ceramide production enhancing effect, and an involucrin expression enhancing effect.

Further, the epidermal cornification improver, the skin moisturizing function improver, the skin barrier function improver, and the skin roughness preventive or improver of the second embodiment of the present invention also contain an extract from *Peristrophe japonica* as an active ingredient. As mentioned above, the transglutaminase activation, the ceramide production enhancement, and the involucrin expression enhancement are significantly important for improvement of epidermal cornification, improvement of skin moisturizing function, maintenance of skin barrier function, and prevention or improvement of skin roughness. Accordingly, the extract from *Peristrophe japonica* having the transglutaminase activation effect, the ceramide production enhancing effect, and the involucrin expression enhancing effect can be contained as the active ingredient in the epidermal cornification improver, the skin moisturizing function improver, the skin barrier function improver and the skin roughness preventive or improver.

Moreover, as mentioned above, ceramides play a role in control of cell proliferation, differentiation, apoptosis and the like. Therefore, the extract from *Peristrophe japonica* that enhances the ceramide production is useful as a drug, a quasi drug or the like for preventing or treating diseases caused by abnormality of cell proliferation or differentiation, such as inflammatory diseases and malignant tumors, by animal cell proliferation inhibition, differentiation induction, apoptosis induction, and the like. Moreover, the extract from *Peristrophe japonica* can also be used for a drug, a quasi drug or the like for preventing or improving bone and joint diseases such as osteoporosis, bone fracture, lumbago and rheumatoid arthritis, or for preventing or improving periodontosis. Further, the extract from *Peristrophe japonica* is also useful as a quasi drug, a cosmetic or the like for providing hair with bounce and resilience or improving the feel of the hair.

Further, as mentioned above, a substance that increases involucrin gene expression can be a wavy hair or curly hair enhancer or a wave formation enhancer. Accordingly, the extract from *Peristrophe japonica* having the involucrin expression enhancing effect can be incorporated as the active ingredient in a wavy hair former. "Wavy hair formation" herein covers enhancement of wavy hair or curly hair or enhancement of wave formation.

In the present specification, "*Peristrophe japonica*" is a plant which belongs to the family Acanthaceae, genus *Peristrophe*.

In manufacture of the extract from *Peristrophe japonica*, an arbitrary part of *Peristrophe japonica* can be used; and an entire plant, a root, a tuberous root, a rhizome, a stock, a branch, a stem, a leaf (a leaf blade, a petiole or the like), a bark, a sap, a resin, a flower (a petal, an ovary or the like), a fruit (a ripe fruit, an unripe fruit or the like), a seed or the like can be used therefor. A plurality of these parts may be used in combination thereof. Above all, the extract from *Peristrophe japonica* to be used in the second embodiment of the present invention is preferably an extract from the entire plant of *Peristrophe japonica*.

The extract from *Justicia procumbens* or *Peristrophe japonica* to be used in the first and second embodiments of the present invention can be obtained by an ordinary extraction method to be applied for extraction from a plant or the like. The extraction method can be appropriately set up, and the extract is preferably obtained by extracting the above-described plant at room temperature or under heating, or using an extraction implement such as a Soxhlet extractor.

In preparation of the extract from *Justicia procumbens* or *Peristrophe japonica*, *Justicia procumbens* or *Peristrophe japonica* can be directly used; or dried and ground, and then used. Moreover, a steam distilled object or pressed object of *Justicia procumbens* or *Peristrophe japonica* can also be used, and as these objects, a purified object from essential oil or the like, or a commercial item can also be used. *Justicia procumbens* or *Peristrophe japonica*, or the steam distilled object or pressed object thereof can be used alone in any one thereof, or in combination of two or more kinds.

An extraction solvent used for preparation of the extract from *Justicia procumbens* or *Peristrophe japonica* can be appropriately selected. Examples thereof include one ordinary used for extracting a plant, such as water; alcohols such as methanol, ethanol, propanol and butanol; polyhydric alcohols such as ethylene glycol, propylene glycol, 1,2-butylene glycol, 1,3-butylene glycol, 1,4-butylene glycol, and 2,3-butylene glycol; ketones such as acetone and methyl ethyl ketone; esters such as methyl acetate and ethyl acetate; linear or cyclic ethers such as tetrahydrofuran and diethyl ether; polyethers such as polyethylene glycol; halogenated hydrocarbons such as dichloromethane, dichloroethane, chloroform, and carbon tetrachloride; hydrocarbons such as hexane, cyclohexane and petroleum ether; aromatic hydrocarbons such as benzene and toluene; pyridines; supercritical carbon dioxide; oils and fats, waxes, and other oils. These may be used alone or in combination of two or more kinds. Above all, water, ethanol or an ethanol aqueous solution is preferred, an ethanol aqueous solution is further preferred, an ethanol aqueous solution having an alcohol content of 30 vol % or more is still further preferred, and an ethanol aqueous solution having an ethanol content of 40 vol % or more is particularly preferred. Moreover, upon extraction, acid, alkali or the like may be added to adjust pH of the extraction solvent.

As extraction conditions, ordinary conditions can also be applied.

For example, in order to obtain the extract from *Justicia procumbens* to be used in the first embodiment of the present invention, *Justicia procumbens* may be subjected to immersion or heating under reflux at 0° C. or higher (preferably 4° C. or higher) and 100° C. or lower (preferably 80° C. or lower, and further preferably 40° C. or lower) for 1 minute or more (preferably 1 hour or more, and further preferably 1 day or more) and 50 days or less (preferably 30 days or less). In order to improve extraction efficiency, stirring may be simultaneously carried out or homogenization treatment may be applied in the solvent. An amount of the extraction solvent to be used is once or more (preferably 5 times or more) and 100 times or less (preferably 50 times of less, further preferably 40 times or less) based on the weight (on dried basis) of *Justicia procumbens*.

Moreover, in order to obtain the extract from *Peristrophe japonica* to be used in the second embodiment of the present invention, *Peristrophe japonica* may be subjected to immersion or heating under reflux at 0° C. or higher and 100° C. or lower for 0.5 hours or more and 30 days or less. In order to improve extraction efficiency, stirring may be simultaneously carried out or homogenization treatment may be applied in the solvent. An amount of the extraction solvent to be used is once or more (preferably 5 times or more) and 100 times or less (preferably 50 times of less, further preferably 40 times or less based on the weight (on dried basis) of *Peristrophe japonica*.

In the present invention, the extract from *Justicia procumbens* or *Peristrophe japonica* may be directly used. Alternatively, a fraction having higher activity obtained by further fractionating the extract by an appropriate separating technique such as gel filtration, chromatography or precision distillation can also be used. Moreover, the extract from *Justicia procumbens* or *Peristrophe japonica* obtained therefrom is diluted, concentrated or freeze-dried, and then prepared in a powder or paste form, and the resultant material can also be used. Moreover, the extract obtained by the above-described method is subjected to solvent substitution using a solvent different from the extraction solvent, and then the resultant material can also be used.

The extract in the present invention includes extracts by various kinds of solvents as obtained by the extraction methods described above, a diluted liquid thereof, a concentrated liquid thereof, a purified fraction thereof, dried powder thereof, or a liquid thereof subjected to solvent substitution.

The transglutaminase activator, the ceramide production enhancer, and the involucrin expression enhancer of the third embodiment of the present invention contain at least one kind of compound represented by Formula (1) as an active ingredient. As verified in Examples described later, the compound represented by Formula (1) has a transglutaminase activation effect, a ceramide production enhancing effect, and an involucrin expression enhancing effect.

Further, the epidermal cornification improver, the skin moisturizing function improver, the skin barrier function improver, and the skin roughness preventive or improver of the third embodiment of the present invention also contain at least one kind of compound represented by Formula (1) as an active ingredient. As mentioned above, the transglutaminase activation, the ceramide production enhancement, and the involucrin expression enhancement are significantly important for improvement of epidermal cornification, improvement of skin moisturizing function, maintenance of skin barrier function, and prevention or improvement of skin roughness. Accordingly, the at least one kind of compound represented by Formula (1) having the transglutaminase activation effect, the ceramide production enhancing effect, and the involucrin expression enhancement enhancing effect can be contained as the active ingredient in the epidermal cornification improver, the skin moisturizing function improver, the skin barrier function improver and the skin roughness preventive or improver.

Moreover, as mentioned above, ceramides play a role in control of cell proliferation, differentiation, apoptosis and the like. Therefore, the compound represented by Formula (1) that enhances the ceramide production is useful as a drug, a quasi drug or the like for preventing or treating diseases caused by abnormality of cell proliferation or differentiation, such as inflammatory diseases and malignant tumors, by animal cell proliferation inhibition, differentiation induction, apoptosis induction, and the like. Moreover, the compound represented by Formula (1) can also be used for a drug, a quasi drug or the like for preventing or improving bone and joint diseases such as osteoporosis, bone fracture, lumbago and rheumatoid arthritis, or for preventing or improving periodontosis. Further, the compound represented by Formula (1) is also useful as a quasi drug, a cosmetic or the like for providing hair with bounce and resilience or improving the feel of the hair.

Further, as mentioned above, a substance that increases involucrin gene expression can be a wavy hair or curly hair enhancer or a wave formation enhancer. Accordingly, the at least one kind of compound represented by Formula (1) having the involucrin expression enhancing effect can be incorporated as the active ingredient in a wavy hair former.

Hereinafter, the compound represented by Formula (1) is described in detail.

In Formula (1), $R_1$ and $R_2$ each independently represent a hydrogen atom, a hydroxyl group, or a linear or branched alkoxy group having 1 to 4 carbon atoms. However, $R_1$ and $R_2$ do not bond with each other to form any ring. $R_1$ and $R_2$ may be the same as or different from each other, but they are preferably the same as each other.

Examples of the alkoxy group represented by $R_1$ and $R_2$ include a methoxy group, an ethoxy group, a n-propoxy group, an iso-propoxy group, n-butoxy group, a tert-butoxy group, a sec-butoxy group and an iso-butoxy group.

$R_1$ and $R_2$ each are preferably a hydrogen atom or a linear or branched alkoxy group having 1 to 4 carbon atoms, more preferably a hydrogen atom or an alkoxy group having 1 or 2 carbon atoms (e.g., a methoxy group, and an ethoxy group), and further preferably a hydrogen atom or a methoxy group.

In Formula (1), $R_3$ represents a hydrogen atom, or a group for forming a methylenedioxy group by bonding with $R_2$. When $R_3$ represents a hydrogen atom, $R_1$ and $R_2$ each are preferably a hydrogen atom, or a linear or branched alkoxy group having 1 to 4 carbon atoms; more preferably a hydrogen atom or an alkoxy group having 1 or 2 carbon atoms; and further preferably a hydrogen atom or a methoxy group. When $R_3$ is bonded with $R_2$ to form a methylenedioxy group, $R_1$ is preferably a hydrogen atom.

In Formula (1), $R_4$ and $R_5$ each represent a hydrogen atom, or a group for forming a methylenedioxy group by bonding with each other. When $R_4$ and $R_5$ are bonded with each other to form a methylenedioxy group, $R_1$ and $R_2$ each are preferably a linear or branched alkoxy group having 1 to 4 carbon atoms, or $R_3$ is preferably a group for forming a methylenedioxy group by bonding with $R_2$.

In Formula (1), $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy. Herein, the hydroxyl group in the sugar residue may form an ester with a carboxylic acid. As the carboxylic acid, a carboxylic acid having 2 to 4 carbon atoms is preferable, and examples thereof include acetic acid, propionic acid, and butyric acid.

Examples of the alkoxy group represented by $R_6$ include a methoxy group, an ethoxy group, a n-propoxy group, an iso-propoxy group, a n-butoxy group, a tert-butoxy group, a sec-butoxy group, an iso-butoxy group, and a pentyloxy group. Of these, an alkoxy group having 1 or 2 carbon atoms (e.g., a methoxy group, or an ethoxy group) is preferable.

Examples of the acyloxy group represented by $R_6$ include a formyloxy group, an acetoxy group, a propionyloxy group, and a butyryloxy group. Of these, an acetoxy group and a propionyloxy group are preferable, and an acetoxy group is more preferable.

When $R_4$ and $R_5$ each are a hydrogen atom, $R_6$ is preferably a hydrogen atom.

In the present invention, as the compound represented by Formula (1), a compound represented by Formula (11), a compound represented by Formula (2), a compound represented by Formula (3), and a compound represented by Formula (4) are preferable.

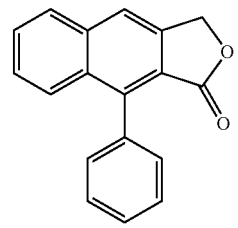

Formula (11)

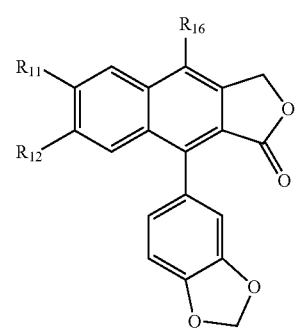

Formula (2)

In Formula (2), $R_{11}$ and $R_{12}$ each independently represent a hydrogen atom, a hydroxyl group, or a linear or branched alkoxy group having 1 to 4 carbon atoms. However, $R_{11}$ and $R_{12}$ do not bond with each other to form any ring. $R_{11}$ and $R_{12}$ may be the same as or different from each other, but they are preferably the same as each other.

Examples of the alkoxy group represented by $R_{11}$ and $R_{12}$ include a methoxy group, an ethoxy group, a n-propoxy group, an iso-propoxy group, a n-butoxy group, a tert-butoxy group, a sec-butoxy group and an iso-butoxy group.

$R_{11}$ and $R_{12}$ each are preferably a linear or branched alkoxy group having 1 to 4 carbon atoms, more preferably an alkoxy group having 1 or 2 carbon atoms (e.g., a methoxy group, and an ethoxy group), and further preferably a methoxy group.

In Formula (2), $R_{16}$ represents a hydrogen atom, a hydroxyl group, a linear or branched alkoxy group having 1 to 5 carbon atoms, or a linear or branched acyloxy group having 1 to 4 carbon atoms. Specific examples and preferable ranges of the alkoxy group and the acyloxy group represented by $R_{16}$ each are the same as those of $R_6$ in Formula (1). $R_{16}$ is preferably a hydrogen atom, a hydroxyl group, an alkoxy group having 1 or 2 carbon atoms, or an acetoxy group.

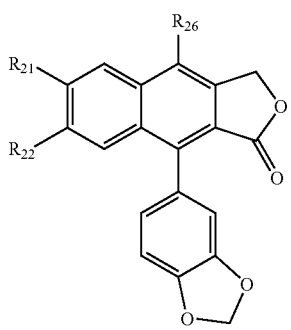

Formula (3)

In Formula (3), $R_{21}$ and $R_{22}$ each independently represent a hydrogen atom, a hydroxyl group, or a linear or branched alkoxy group having 1 to 4 carbon atoms. However, $R_{21}$ and $R_{22}$ do not bond with each other to form any ring. $R_{21}$ and $R_{22}$ may be the same as or different from each other, but they are preferably the same as each other.

Examples of the alkoxy group represented by $R_{21}$ and $R_{22}$ include a methoxy group, an ethoxy group, a n-propoxy group, an iso-propoxy group, a n-butoxy group, a tert-butoxy group, a sec-butoxy group and an iso-butoxy group.

$R_{21}$ and $R_{22}$ each are preferably a linear or branched alkoxy group having 1 to 4 carbon atoms, more preferably an alkoxy group having 1 or 2 carbon atoms (e.g., a methoxy group, and an ethoxy group), and further preferably a methoxy group.

In Formula (3), $R_{26}$ represents a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy. Herein, the hydroxyl group in the sugar residue may form an ester with a carboxylic acid. As the carboxylic acid, a carboxylic acid having 2 to 4 carbon atoms is preferable, and examples thereof include acetic acid, propionic acid, and butyric acid.

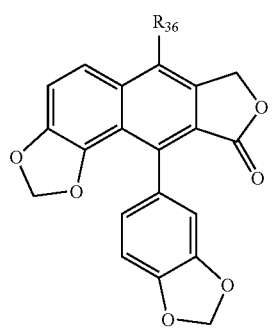

Formula (4)

In Formula (4), $R_{36}$ represents a hydrogen atom, a hydroxyl group, a linear or branched alkoxy group having 1 to 5 carbon atoms, or a linear or branched acyloxy group having 1 to 4 carbon atoms. Specific examples and preferable ranges of the alkoxy group and the acyloxy group represented by $R_{36}$ each are the same as those of $R_6$ in Formula (1). $R_{36}$ is preferably a hydrogen atom or a hydroxyl group, and more preferably a hydroxyl group.

Hereinafter, specific examples of the compound represented by Formula (1) are shown, but the present invention is not limited thereto.

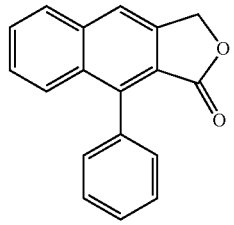

(11)

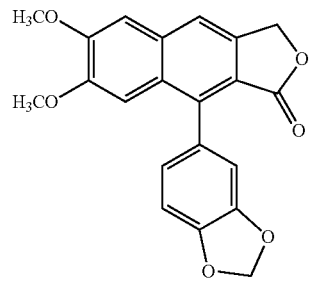

(12)

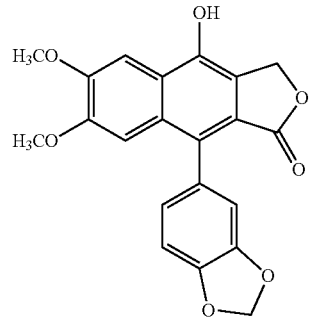

(13)

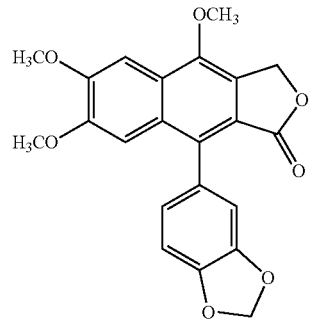

(14)

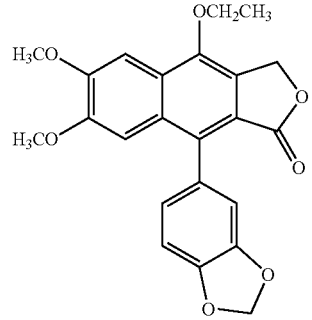

(15)

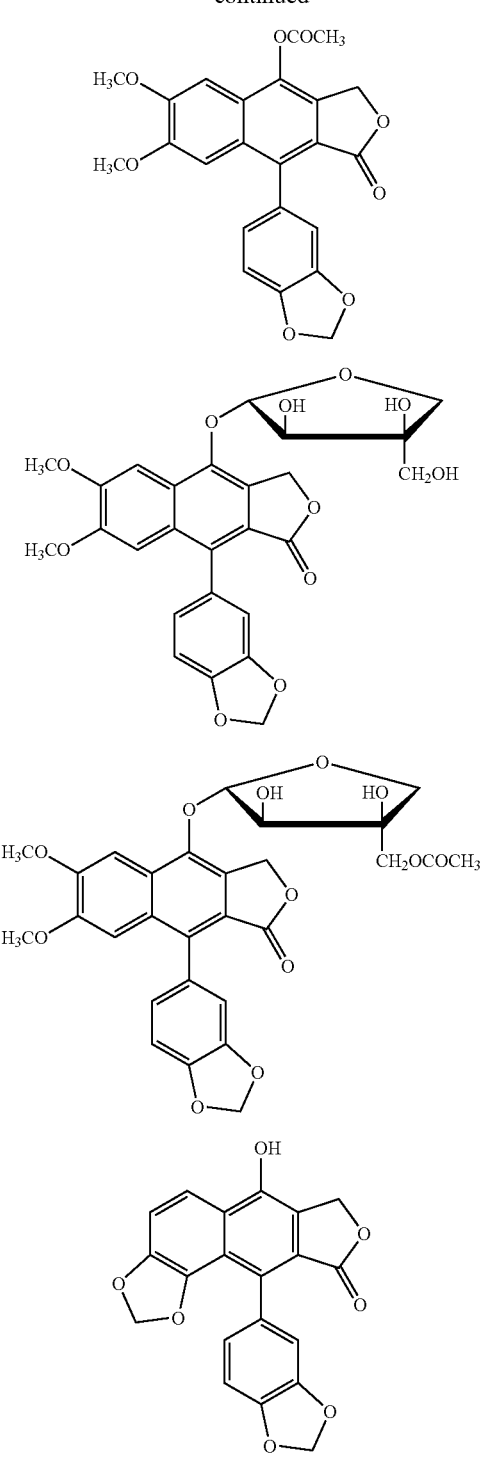

Exemplified compound (11): 9-phenylnaphtho[2,3-c]furan-1(3H)-one

Exemplified compound (12): Justicidin B (6,7-dimethoxy-9-(1,3-benzodioxol-5-yl)naphtho[2,3-c]furan-1(3H)-one)

Exemplified compound (13): Diphyllin (4-hydroxy-6,7-dimethoxy-9-(1,3-benzodioxol-5-yl)naphtho[2,3-c]furan-1(3H)-one)

Exemplified compound (14): Justicidin A (4,6,7-trimethoxy-9-(1,3-benzodioxol-5-yl)naphtho[2,3-c]furan-1(3H)-one)

Exemplified compound (15): 4-ethoxy-6,7-dimethoxy-9-(1,3-benzodioxol-5-yl)naphtho[2,3-c]furan-1(3H)-one Exemplified compound (16): 4-acetoxy-6,7-dimethoxy-9-(1,3-benzodioxol-5-yl)naphtho[2,3-c]furan-1(3H)-one Exemplified compound (17): Tuberculatin ((−)-4-[(D-apio-β-D-furanosyl)oxy]-9-(1,3-benzodioxol-5-yl)-6,7-dimethoxy-1H-naphtho[2,3-c]furan-3-one)

Exemplified compound (18): Tuberculatin-5″-acetate

Exemplified compound (19): Justirumarin (furo[3',4',6,7]naphtho[1,2-d]-1,3-dioxole-9(7H)-one)

In the transglutaminase activator, the ceramide production enhancer, the involucrin expression enhancer, the epidermal cornification improver, the skin moisturizing function improver, the skin barrier function improver, the skin roughness preventive or improver, and the wavy hair former in the third embodiment of the present invention, as the active ingredient, the compound represented by Formula (1) may be used alone in one kind or in combination of two or more kinds thereof.

The compound represented by Formula (1) can be synthesized according to an ordinary method. As the method of synthesizing the compound represented by Formula (1), the compound can be synthesized according to the method described in J. Org. Chem., 1996, vol. 61, pp. 3452-3457, Med. Chem. Res., 2010, vol. 19, pp. 71-76, The Fifth Series of Experimental Chemistry (Jikken Kagaku Koza, 5$^{th}$ edition, in Japanese), p. 42, or the like.

Synthesis examples of the compound represented by Formula (1) are shown below.

Synthesis Example of Exemplified Compound (13)

The exemplified compound (13) can be synthesized by allowing an acetal compound obtained from a reaction between 2-bromo-5,6-dimethoxybenzaldehyde and ethylene glycol to react with 3,4-(methylenedioxy)benzaldehyde under basic conditions, and further carrying out a reaction in the presence of DEADC (diethylacetylene carboxylate) under heating conditions, and finally carrying out reduction by NaBH$_4$.

Synthesis Example of Exemplified Compound (12)

The exemplified compound (12) can be obtained by allowing an acetal compound obtained from a reaction between 2-bromo-5,6-dimethoxybenzaldehyde and ethylene glycol to react with 3,4-(methylenedioxy)benzaldehyde under basic conditions, and heating the resultant reaction product in the presence of maleic anhydride under acidic conditions while heating, and finally carrying out reduction by NaBH$_4$.

Synthesis Example of Exemplified Compound (14)

The exemplified compound (14) can be obtained by acting methyl iodide on the exemplified compound (13) under basic conditions.

Synthesis Example of Exemplified Compound (15)

The exemplified compound (15) can be obtained by adding bromoalkane to the exemplified compound (13) under basic conditions.

Synthesis Example of Exemplified Compound (16)

The exemplified compound (16) can be obtained by using the exemplified compound (13) as a starting material, and acylating a hydroxy group of the exemplified compound (13) by an ordinary acylation method.

In the present invention, as the compound represented by Formula (1), a commercial item may be obtained and used. Examples of the commercialized product of the compound represented by Formula (1) include catalog No. ST077116 from TimTec Inc.; catalog Nos. P2000N-07371, P2000N-22338 and P2000N-10719 from Pharmeks LTD.; and catalog No. ABS-00020012-001 from ChromaDex Inc.

The compound represented by Formula (1) can be isolated from an extract from a plant, such as *Peristrophe japonica*, *Justicia procumbens*, *Haplophyllum patavinum* and *Cleistanthus Collinus*.

In manufacture of the extract, an arbitrary part of the above-described plant can be used, and an entire plant, a root, a tuberous root, a rhizome, a stock, a branch, a stem, a leaf (a leaf blade, a petiole or the like), a bark, a sap, a resin, a flower (a petal, an ovary or the like), a fruit (a ripe fruit, an unripe fruit or the like), a seed or the like can be used therefor. A plurality of these parts may be used in combination thereof.

The extract can be obtained by an ordinary extraction method to be applied for extraction from a plant or the like. The extraction method can be appropriately set up, and the extract is preferably obtained by extracting the above-described plant at room temperature or under heating, or using an extraction implement such as a Soxhlet extractor.

In preparation of the extract, the above-described plant can be directly used, or dried and ground, and then used. Moreover, a steam distilled object or pressed object of the above-described plant can also be used, and as these objects, a purified object from essential oil or the like, or a commercial item can also be used. The above-described plant, or the steam distilled object or pressed object thereof can be used alone in any one thereof, or in combination of two or more kinds.

An extraction solvent used for preparation of the extract can be appropriately selected. Examples thereof include one ordinary used for extracting a plant, for example water; alcohols such as methanol, ethanol, propanol and butanol; polyhydric alcohols such as ethylene glycol, propylene glycol, 1,2-butylene glycol, 1,3-butylene glycol, 1,4-butylene glycol, and 2,3-butylene glycol; ketones such as acetone and methyl ethyl ketone; esters such as methyl acetate and ethyl acetate; linear or cyclic ethers such as tetrahydrofuran and diethyl ether; polyethers such as polyethylene glycol; halogenated hydrocarbons such as dichloromethane, dichloroethane, chloroform, and carbon tetrachloride; hydrocarbons such as hexane, cyclohexane and petroleum ether; aromatic hydrocarbons such as benzene and toluene; pyridines; supercritical carbon dioxide; oils and fats, waxes, and other oils. These may be used alone or in combination of two or more kinds. Above all, water, ethanol or an ethanol aqueous solution is preferred, an ethanol aqueous solution is further preferred, an ethanol aqueous solution having an alcohol content of 30 vol % or more is still further preferred, and an ethanol aqueous solution having an ethanol content of 40 vol % or more is particularly preferred. Moreover, upon extraction, acid, alkali or the like may be added to adjust pH of the extraction solvent.

The above-described extraction means can be appropriately selected, and examples include liquid-liquid extraction, solid-liquid extraction, immersion, infusion, decoction, reflux extraction, ultrasonic extraction, microwave extraction, and centrifugal extraction. They may be used singly or in combinations of two or more. At this time, a batch type extractor, Soxhlet extractor, or the like, may be used. Moreover, the extraction may be carried out under a nonoxidative atmosphere, while dissolved oxygen is removed by boiling and degassing the extract or passing an inert gas such as a nitrogen gas therethrough.

The above-prepared extract may be directly used. Alternatively, the above-prepared extract may be subjected to fractionating by an appropriate separating technique such as gel filtration, chromatography or precision distillation can also be used. Moreover, the obtained extract may be diluted, concentrated or freeze-dried, and then prepared in a powder or paste form.

When the compound represented by Formula (1) is isolated from the extract from *Justicia procumbens* or *Peristrophe japonica*, the compound represented by Formula (1) can be obtained by purifying the extracts from these plants by column chromatography or the like. More specifically, the compound represented by Formula (1) can be obtained by extracting a material obtained by drying or grinding an arbitrary part (for example, entire plant) of *Peristrophe japonica* or *Justicia procumbens*, when necessary, and concentrating the resultant extract or removing impurities from the extract, and then purifying the resultant material by the column chromatography. Specific examples of the compound represented by Formula (1) isolated from the extracts from these plants include the exemplified compound (12), the exemplified compound (14) and the exemplified compound (17).

Isolation of the compound (1) represented by Formula (1) from an extract from *Haplophyllum patavinum* or *Cleistanthus Collinus* may be carried out according to the methods described in Chem. Pharm. Bull., 2002, vol. 50, pp. 844-846, Tetrahedron, 1969, vol. 25, pp. 2815-2821, or the like. Specific examples of the compound represented by Formula (1) isolated from the extracts from these plants include the exemplified compound (12) and the exemplified compound (13).

A method of purifying the extract from *Peristrophe japonica* or *Justicia procumbens* by the column chromatography or the like to isolate the compound represented by Formula (1) will be described.

The extract from *Peristrophe japonica* or *Justicia procumbens* obtained according to the above-described procedure, or an extract subjected to further extraction or liquid-liquid distribution, when necessary, by the above-described addition solvent is subjected to the column chromatography using silica gel or the like. In the column chromatography, for example, a gradient is applied, using hexane-ethyl acetate, from 0% to 100% in an ethyl acetate percentage over 60 minutes, and then, a gradient is applied, using ethyl acetate-methanol, from 0% to 10% in a methanol percentage over 30 minutes, and then elution is carried out using 100% methanol for 30 minutes, and on the occasion, fractions eluted by 100% methanol from a vicinity of a ratio of 1/9 in hexane/ethyl acetate may be collected. The fractions can be separated into one insoluble in methanol and one soluble in methanol. The one insoluble in methanol is subjected to inverse phase HPLC in a two-phase system of 0.1% formic acid aqueous solution-acetonitrile, and fractions eluted near 10 to 15 minutes by elution using 50% acetonitrile for 20 minutes may be collected. On the other hand, the one soluble in methanol is subjected to inverse phase HPLC in a two-phase system of 0.1% formic acid aqueous solution-acetonitrile, and fractions eluted near 12 to 15 minutes by elution using 35% acetonitrile for 16 minutes may be collected.

The fraction can be confirmed to contain the compound represented by Formula (1) by measuring transglutaminase activity of the fraction obtained, when necessary. A method of measuring the transglutaminase activity may be applied according to the method described in Examples later, for example.

A form of the transglutaminase activator, the ceramide production enhancer, the involucrin expression enhancer, the epidermal cornification improver, the skin moisturizing function improver, the skin barrier function improver, the horny cell layer moisture content increasing agent, the horny cell layer moisture reduction inhibitor, the skin roughness preventive or improver, and the wavy hair former of the present invention can be appropriately selected, and such a product may be processed into a medical composition, a cosmetic composition or a food composition, and may be incorporated thereinto.

When the medical composition is prepared, the composition is ordinarily prepared as a preparation containing the above-described active ingredient and preferably a pharmaceutically acceptable carrier. The pharmaceutically acceptable carrier generally means an inert, nontoxic, solid or liquid extender, diluent, encapsulation material or the like that does not react with the above-described active ingredient, and specific examples include a solvent or a dispersion medium such as water, ethanol, polyols (propylene glycol, butylene glycol, glycerin and polyethylene glycol), a suitable mixture thereof and vegetable oil.

The medical composition is orally or parenterally administered into, for example, an oral cavity, a skin, a hypodermis, a mucosa, a vein, an artery, a muscle, an abdominal cavity, a vagina, a lung, a brain, an eye or a nasal cavity. Specific examples of orally administrable preparations include a tablet, a granule, a fine granule, powder, a capsule, a chewable agent, a pellet, a syrup, a liquid, a suspension and an inhalation. Specific examples of parenterally administrable preparations include a suppository, a retention type clyster, a drop, an ophthalmic solution, a nasal drop, a pessary, an injection and an oral-cavity cleaner, and a skin external preparation such as an ointment, a cream pharmaceutical, a gel, a controlled release patch agent and a patch. The medical composition may be parenterally administered in the form of a sustained-release hypodermic implant or a target transmission system (for example, a monoclonal antibody, a vector transmission, ion implantation, a polymer matrix, a liposome and a microsphere).

The medical composition may further contain a conventional additive in a medicine field. Examples of such an additive include an excipient, a binder, a disintegrator, a lubricant, an antioxidant, a colorant and a corrigent. The additive can be used when necessary. In order to achieve sustained release such that the composition can be effected for a long time, the composition can also be coated with a known retardant or the like. As the excipient, for example, sodium carboxymethylcellulose, agar, light anhydrous silicic acid, gelatin, crystalline cellulose, sorbitol, talc, dextrin, starch, milk sugar, white soft sugar, glucose, magnesium meta-aluminosilicate, calcium hydrogen phosphate or the like can be used. Examples of the binder include gum arabic, sodium alginate, ethyl cellulose, casein sodium, sodium carboxymethylcellulose, agar, purified water, gelatin, starch, tragacanth, and milk sugar. Examples of the disintegrator include carboxymethylcellulose, sodium carboxymethylcellulose, calcium carboxymethylcellulose, crystalline cellulose, starch, and hydroxypropyl starch. Examples of the lubricant include stearic acid, calcium stearate, magnesium stearate, talc, hardened oil, sucrose esters of fatty acids, and waxs. Examples of the antioxidant include tocopherol, esters of gallic acid, dibutylhydroxytoluene (BHT), butylated hydroxyanisole (BHA), and ascorbic acid. Other additives or chemicals may be added thereto, when necessary, for example, an antacid (e.g. sodium hydrogencarbonate, magnesium carbonate, precipitated calcium carbonate and synthetic hydrotalcite) or a gastric mucosa protective agent (e.g. synthetic aluminum silicate, sucralfate and sodium copper chlorophyllin) may be added thereto.

When the cosmetic composition is prepared, a form thereof can be appropriately selected. The cosmetic composition can be processed into an arbitrary form, such as a solution, a milky lotion, powder, a water-oil two-phase system, a water-oil-powder three-phase system, a gel, a solid such as a tablet, aerosol, mist, a capsule and a sheet. Moreover, a product form of the cosmetic composition is also arbitrary, and specific examples include a skin care cosmetic product such as a facial wash, a makeup remover, a skin lotion, a serum, a pack, a milky lotion, a cream, and a sun screen; a makeup cosmetic product such as a foundation cream, a makeup base, a lipstick, an eye shadow, an eyeliner, a mascara, an eyebrow pencil, a rouge and a nail enamel; a hair cosmetic product such as a hair shampoo, a hair rinse, a charge for a haircut, a hair dye, and a hair restorer; a body cleansing preparation such as a soap, a body soap, a deodorant cosmetic product and a bath agent; an oral cavity cosmetic material such as a tooth paste and a mouth wash; and aromatic cosmetic product such as a perfume. Moreover, this cosmetic product may belong to either the cosmetic or the quasi drug according to the Pharmaceutical Affairs Law of Japan.

The cosmetic composition can be manufactured by an ordinary method by formulating any other ingredient that is conventionally used for the cosmetic, the quasi drug and the medical product, for example, a powder ingredient, a liquid fat and oil, a solid fat and oil, a wax, a hydrocarbon, a higher fatty acid, a higher alcohol, an ester, silicone, an anionic surfactant, a cationic surfactant, an amphoteric surfactant, a nonionic surfactant, a moisturizer, a water soluble polymer, a thickening agent, a film forming agent, an ultraviolet light absorber, a sequestering agent, lower alcohol, polyhydric alcohol, sugar, an amino acid, an organic amine, a polymer emulsion, a pH adjuster, a skin dietetical agent, a vitamin, an antioxidant, an antioxidant aid, a perfume and water, when necessary.

Specific examples of other ingredients that can be formulated into the cosmetic composition include a preservative (e.g. ethyl paraben and butyl paraben), an antiphlogistic (e.g. a glycyrrhizin acid derivative, a glycyrrhetinic acid derivative, a salicylic acid derivative, cypress thiol, zinc oxide and allantoin), a skin whitening agent (e.g. ascorbic acid and a derivative thereof, a placenta extract, an extract from *Saxifraga stolonifera*, and arbutin), various kinds of extracts (e.g. *Phellodendron amurense, Coptis japonica, Lithospermum erythrorhizon, Paeonia lactiflora, Swertia japonica*, birch, sage, *Eriobotrya japonica*, carrot, aloe, mallow, iris, grape, *Coix lachryma-jobi*, sponge gourd, lily, saffron, *Cnidium officinale*, ginger, *Hypericum erectum, Ononis spinosa*, garlic, red pepper, *Aurantii nobllis* pericarpium, angericae radix and marine algae), an activator agent (e.g. royal jelly, photosensitive base and a cholesterol derivative), a blood circulation accelerator (e.g. nonylic acid vanillylamide, nicotinic acid benzyl ester, nicotinic acid β-butoxy ethyl ester, capsaicin, zingerone, *Tinctura cantharidis*, ichthammol, tannic acid, α-borneol, tocopherol nicotinate, inositol hexanicotinate, cyclandelate, cinnarizine, tolazoline, acetylcholine, verapamil, cepharanthin, and γ-orizanol), an antiseborrheic drug (e.g. sulfur and thianthol), an anti-inflammatory agent (e.g. tranexamic acid, thiotaurine and hypotaurine) and a germicide (e.g. triclosan, cetylpyridinium chloride, Timors and benzalkonium chloride).

The above-described medical composition and cosmetic composition can be applied in the form of a stomatological composition, an external application composition, an internal application composition or the like; and preferably used in the form of a skin external application composition.

When the composition is used in the form of the skin external application composition, the composition can be appropriately formulated with, in addition to the above-described active ingredient, an ingredient used for an ordinary skin external application composition, such as a surfactant, an oil substance, a polymer compound, a preservative, various kinds of medicinal ingredients, powder, an ultraviolet light absorber, a dye, a flavoring agent, an emulsion stabilizer and a pH adjuster. Specific examples of the medicinal ingredient include, in the case of the epidermal cornification improver or the skin moisturizing function improver, vitamin D3, a sphingosine derivative, oleanolic acid, clofibric acid and oleic ethanolamide.

When the food composition is prepared, a form thereof can be appropriately selected, and the form also includes a beverage. The form includes a general food, and also food and drink indicating the effect of treatment, prevention, improvement or the like of a disease or condition that can be treated, prevented or improved by any one of improvement of the epidermal cornification, improvement and maintenance of the skin moisturizing function or barrier function, or the like, the transglutaminase activation, the ceramide production enhancement and the involucrin expression enhancement. More specifically, the form includes a health food, a physiologically functional food, a food for sick people and a food for specified health use. The health food, the physiologically functional food, the food for sick person and the food for specified health use can be used, specifically, in the form of various kinds of preparations such as a fine granule, a tablet, a granule, powder, a capsule, a syrup, a liquid and a liquid diet, and can be used for these preparations. The food composition in the form of the preparation can be manufactured, in a manner similar to a medical preparation, by mixing the above-described active ingredient and a carrier acceptable as the food, and for example, a suitable excipient (e.g. starch, processed starch, lactose, glucose or water) and so forth, and applying a conventional means. Further, the food composition can take a form of a liquid food composition such as soups, juices, a milk beverage, a tea beverage, a coffee beverage, a cocoa beverage and a jelly-like beverage; a semi-solid food composition such as pudding and yogurt; breads; noodles such as flour noodles; confectionaries such as a cookie, a chocolate, a candy and a gum; and spreads such as rice seasoning mix, butter and jam. Moreover, the food includes a fodder.

The food composition may be formulated with various kinds of food additives alone or in combination thereof, such as an antioxidant, a spice, various kinds of esters, organic acids, organic acid salts, inorganic acids, inorganic acid salts, dyes, an emulsifier, a preservative, a condiment, a sweetener, an acidulant, fruit-juice extracts, vegetable extracts, nectar extracts, a pH adjuster and a quality stabilizer.

An administration object of the transglutaminase activator, the ceramide production enhancer, the involucrin expression enhancer, the epidermal cornification improver, the skin moisturizing function improver, the skin barrier function improver, the horny cell layer moisture content increasing agent, the horny cell layer moisture content reduction inhibitor, the skin roughness preventive or improver, or the wavy hair former of the present invention is preferably a warm-blooded vertebrate, and further preferably a mammal. Specific examples of the mammals herein include a human and a non-human mammal such as a monkey, a mouse, a rat, a rabbit, a dog, a cat, a bovine, a horse and a pig. The transglutaminase activator, the ceramide production enhancer, the involucrin expression enhancer, the epidermal cornification improver, the skin moisturizing function improver, the skin barrier function improver, the horny cell layer moisture content increasing agent, the horny cell layer moisture content reduction inhibitor, the skin roughness preventive or improver, or the wavy hair former of the present invention is preferably administered to primates such as a human and a monkey, and particularly preferably to a human.

The above-described active ingredient used in the present invention, and the transglutaminase activator, the ceramide production enhancer, the involucrin expression enhancer, the epidermal cornification improver, the skin moisturizing function improver, the skin barrier function improver, the horny cell layer moisture content increasing agent, the horny cell layer moisture content reduction inhibitor, the skin roughness preventive or improver, or the wavy hair former of the present invention can be applied to a subject who desires prevention or treatment of epidermal incomplete cornification, improvement of the skin moisturizing or skin barrier function, an increase in the horny cell layer moisture content, inhibition of the horny cell layer moisture content reduction, prevention or improvement of the skin roughness, or formation of the wavy hair. The above-described active ingredient or agent is preferably applied under necessary conditions (preferably under conditions of low humidity and dryness). Moreover, the above-described active ingredient or agent is preferably applied to a skin, scalp or hair.

An applied dose of the above-described active ingredient in the transglutaminase activator, the ceramide production enhancer, the involucrin expression enhancer, the epidermal cornification improver, the skin moisturizing function improver, the skin barrier function improver, the horny cell layer moisture content increasing agent, the horny cell layer moisture content reduction inhibitor, the skin roughness preventive or improver, or the wavy hair former of the present invention can be appropriately determined depending on conditions, body weight, sex or age of an individual, activity of a raw material, an administration or ingestion route, an administration or ingestion schedule, a preparation form, or other factors.

For example, in the first and second embodiments of the present invention, the dose is preferably 0.001 mg or more and 1 g or less, or preferably from 0.001 to 1 mg, per day and per 1 kg body weight, based on the mass of the above-described active ingredient. Moreover, in the third embodiment of the present invention, the dose is preferably $1.0 \times 10^{-7}$ mg or more, more preferably $1.0 \times 10^{-6}$ mg or more, and preferably 0.1 g or less, more preferably 0.001 mg or less, or preferably from $1.0 \times 10^{-7}$ to 0.1 mg, and more preferably from $1.0 \times 10^{-6}$ to 0.001 mg, per day and per adult (body weight: 60 kg), based on the mass of the above-described active ingredient.

Moreover, the above-described active ingredient can be ingested or administered once a day or divisionally several times a day or during an arbitrary period or at intervals.

A content of the above-described active ingredient in the transglutaminase activator, the ceramide production enhancer, the involucrin expression enhancer, the epidermal cornification improver, the skin moisturizing function improver, the skin barrier function improver, the horny cell layer moisture content increasing agent, the horny cell layer moisture content reduction inhibitor, the skin roughness preventive or improver, or the wavy hair former of the present invention can be appropriately determined so as to attain the above-described dose.

For example, in the transglutaminase activator, the ceramide production enhancer, the involucrin expression enhancer, the epidermal cornification improver, the skin moisturizing function improver, the skin barrier function improver, the horny cell layer moisture content increasing agent, the horny cell layer moisture content reduction inhibitor, the skin roughness preventive or improver, or the wavy hair former of the first and second embodiments of the present invention, the content of the active ingredient is preferably 0.00001 mass % or more, more preferably 0.0001 mass % or more, and further preferably 0.0005 mass % or more; preferably 20 mass % or less, more preferably 10 mass % or less, and further preferably 5 mass % or less; and from 0.00001 to 20 mass %, more preferably from 0.0001 to 10 mass %, and further preferably from 0.0005 to 5 mass %.

Further, in the transglutaminase activator, the ceramide production enhancer, the involucrin expression enhancer, the epidermal cornification improver, the skin moisturizing function improver, the skin barrier function improver, the skin roughness preventive or improver, or the wavy hair former of the third embodiment of the present invention, the content of the active ingredient is preferably $1.0 \times 10^{-19}$ mass % or more, more preferably $1.0 \times 10^{-9}$ mass % or more, and further preferably $1.0 \times 10^{-9}$ mass % or more; preferably 0.01 mass % or less, more preferably 0.005 mass % or less, further preferably 0.001 mass % or less, and particularly preferably $1.0 \times 10^{-4}$ mass % or less.

With regard to the embodiments described above, also disclosed by the present invention includes a transglutaminase activator described below, a ceramide production enhancer described below, an involucrin expression enhancer described below, an epidermal cornification improver described below, a skin moisturizing function improver described below, a skin barrier function improver described below, a horny cell layer moisture content increasing agent described below, a horny cell layer moisture content reduction inhibitor described below, a skin roughness preventive or improver described below, a wavy hair former described below, a production method described below, a method described below, and use described below.

<1> A transglutaminase activator containing at least one kind selected from the group consisting of an extract from *Justicia procumbens*, an extract from *Peristrophe japonica*, and a compound represented by Formula (1), as an active ingredient.

<2> A ceramide production enhancer containing at least one kind selected from the group consisting of an extract from *Justicia procumbens*, an extract from *Peristrophe japonica*, and a compound represented by Formula (1), as an active ingredient.

<3> An involucrin expression enhancer containing at least one kind selected from the group consisting of an extract from *Peristrophe japonica*, and a compound represented by Formula (1), as an active ingredient.

<4> An epidermal cornification improver containing at least one kind selected from the group consisting of an extract from *Justicia procumbens*, an extract from *Peristrophe japonica*, and a compound represented by Formula (1), as an active ingredient.

<5> A skin moisturizing function improver containing at least one kind selected from the group consisting of an extract from *Justicia procumbens*, an extract from *Peristrophe japonica*, and a compound represented by Formula (1), as an active ingredient.

<6> A skin barrier function improver containing at least one kind selected from the group consisting of an extract from *Justicia procumbens*, an extract from *Peristrophe japonica*, and a compound represented by Formula (1), as an active ingredient.

<7> A skin roughness preventive or improver containing at least one kind selected from the group consisting of an extract from *Justicia procumbens*, an extract from *Peristrophe japonica*, and a compound represented by Formula (1), as an active ingredient.

<8> A wavy hair former containing at least one kind selected from the group consisting of an extract from *Peristrophe japonica*, and a compound represented by Formula (1), as an active ingredient.

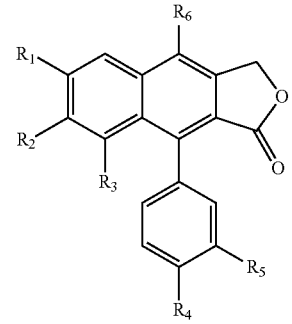

Formula (1)

(In Formula (1), $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid (preferably a carboxylic acid having 2 to 4 carbon atoms).)

<9> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <1> to <8>, wherein the compound represented by Formula (1) is a compound represented by Formula (11), or a compound represented by any one of Formulas (2) to (4):

Formula (11)

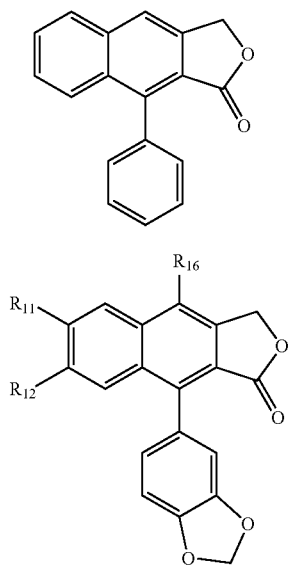

Formula (2)

Formula (3)

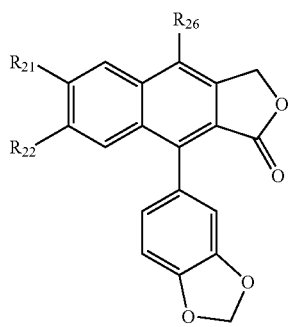

wherein, in Formula (2), $R_{11}$ and $R_{12}$ each independently represent a hydrogen atom, a hydroxyl group, or a linear or branched alkoxy group having 1 to 4 carbon atoms (preferably a linear or branched alkoxy group having 1 to 4 carbon atoms, more preferably an alkoxy group having 1 or 2 carbon atoms, and further preferably a methoxy group); $R_{16}$ represents a hydrogen atom, a hydroxyl group, a linear or branched alkoxy group having 1 to 5 carbon atoms, or a linear or branched acyloxy group having 1 to 4 carbon atoms (preferably a hydrogen atom, a hydroxyl group, an alkoxy group having 1 or 2 carbon atoms, or an acetoxy group);

wherein, in Formula (3), $R_{21}$ and $R_{22}$ each independently represent a hydrogen atom, a hydroxyl group, or a linear or branched alkoxy group having 1 to 4 carbon atoms (preferably a linear or branched alkoxy group having 1 to 4 carbon atoms, more preferably an alkoxy group having 1 or 2 carbon atoms, and further preferably a methoxy group); $R_{26}$ represents a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid (preferably a carboxylic acid having 2 to 4 carbon atoms); and Formula (4)

wherein, in Formula (4), $R_{36}$ represents a hydrogen atom, a hydroxyl group, a linear or branched alkoxy group having 1 to 5 carbon atoms, or a linear or branched acyloxy group having 1 to 4 carbon atoms (preferably a hydrogen atom or a hydroxyl group, and more preferably a hydroxyl group).

<10> Use of at least one kind selected from the group consisting of an extract from *Justicia procumbens*, an extract from *Peristrophe japonica*, and a compound represented by Formula (1), as a transglutaminase activator or a ceramide production enhancer.

<11> Use of at least one kind selected from the group consisting of an extract from *Justicia procumbens*, an extract from *Peristrophe japonica*, and a compound represented by Formula (1), in the manufacture of a transglutaminase activator or a ceramide production enhancer.

<12> A method of using at least one kind selected from the group consisting of an extract from *Justicia procumbens*, an extract from *Peristrophe japonica*, and a compound represented by Formula (1), as a transglutaminase activator or a ceramide production enhancer.

<13> A method of activating transglutaminase or a method of enhancing ceramide production, using at least one kind selected from the group consisting of an extract from *Justicia procumbens*, an extract from *Peristrophe japonica*, and a compound represented by Formula (1).

<14> Use of at least one kind selected from the group consisting of an extract from *Peristrophe japonica*, and a compound represented by Formula (1), as an involucrin expression enhancer.

<15> Use of at least one kind selected from the group consisting of an extract from *Peristrophe japonica*, and a compound represented by Formula (1), in the manufacture of an involucrin expression enhancer.

<16> A method of using at least one kind selected from the group consisting of an extract from *Peristrophe japonica*, and a compound represented by Formula (1), as an involucrin expression enhancer.

<17> A method of enhancing involucrin expression, using at least one kind selected from the group consisting of an extract from *Peristrophe japonica*, and a compound represented by Formula (1).

<18> Use of at least one kind selected from the group consisting of an extract from *Justicia procumbens*, an extract from *Peristrophe japonica*, and a compound represented by Formula (1), as an epidermal cornification improver, a skin moisturizing function improver, a skin barrier function improver, or a skin roughness preventive or improver.

<19> Use of at least one kind selected from the group consisting of an extract from *Justicia procumbens*, an extract from *Peristrophe japonica*, and a compound represented by Formula (1), in the manufacture of an epidermal cornification improver, a skin moisturizing function improver, a skin barrier function improver, or a skin roughness preventive or improver.

<20> A method of using at least one kind selected from the group consisting of an extract from *Justicia procumbens*, an extract from *Peristrophe japonica*, and a compound represented by Formula (1), as an epidermal cornification improver, a skin moisturizing function improver, a skin barrier function improver, or a skin roughness preventive or improver.

<21> A method of improving epidermal cornification, a method of improving a skin moisturizing function, a method of improving a skin barrier function, or a method of preventing or improving skin roughness, containing administering at least one kind selected from the group consisting of an extract from *Justicia procumbens*, an extract from *Peristrophe japonica*, and a compound represented by Formula (1).

<22> At least one kind selected from the group consisting of an extract from *Justicia procumbens*, an extract from *Peristrophe japonica*, and a compound represented by Formula (1) for use in the method of preventing or treating the epidermal incomplete cornification of the skin, the method of improving the skin moisturizing function, the method of improving the skin barrier function, or the method of preventing or improving the skin roughness.

<23> Use of at least one kind selected from the group consisting of an extract from *Justicia procumbens*, an extract from *Peristrophe japonica*, and a compound represented by Formula (1), in the manufacture of a drug for preventing or treating epidermal incomplete cornification of a skin, a drug for improving a skin moisturizing function, a drug for improving a skin barrier function, or a drug for preventing or improving skin roughness.

<24> Use of at least one kind selected from the group consisting of an extract from *Justicia procumbens*, an extract from *Peristrophe japonica*, and a compound represented by Formula (1), for applying to a non-therapeutic method of treating epidermal incomplete cornification of a skin, a skin moisturizing function, a skin barrier function, or skin roughness.

<25> Use of at least one kind selected from the group consisting of an extract from *Peristrophe japonica*, and a compound represented by Formula (1), as a wavy hair former.

<26> Use of at least one kind selected from the group consisting of an extract from *Peristrophe japonica*, and a compound represented by Formula (1), in the manufacture of a wavy hair former.

<27> A method of using at least one kind selected from the group consisting of an extract from *Peristrophe japonica*, and a compound represented by Formula (1), as a wavy hair former.

<28> A method of forming wavy hair, containing administering at least one kind selected from the group consisting of an extract from *Peristrophe japonica*, and a compound represented by Formula (1)

<29> At least one kind selected from the group consisting of an extract from *Peristrophe japonica* and a compound represented by Formula (1), for applying to a method of forming wavy hair.

<30> At least one kind selected from the group consisting of an extract from *Peristrophe japonica* and a compound represented by Formula (1), for manufacture of drug for forming wavy hair.

<31> Use of at least one kind selected from the group consisting of an extract from *Peristrophe japonica* and a compound represented by Formula (1), for applying to a non-therapeutic method of treating wavy hair formation.

<32> The use or method described in any one of the above items <10> to <31>, wherein the compound represented by Formula (1) is a compound represented by Formula (11), or a compound represented by any one of Formulas (2) to (4).

<1-1> A transglutaminase activator containing an extract from *Justicia procumbens*, as an active ingredient.

<1-2> A ceramide production enhancer containing an extract from *Justicia procumbens*, as an active ingredient.

<1-3> An epidermal cornification improver containing an extract from *Justicia procumbens*, as an active ingredient.

<1-4> A skin moisturizing function improver containing an extract from *Justicia procumbens*, as an active ingredient.

<1-5> A skin barrier function improver containing an extract from *Justicia procumbens*, as an active ingredient.

<1-6> A horny cell layer moisture content increasing agent containing an extract from *Justicia procumbens*, as an active ingredient.

<1-7> A horny cell layer moisture content reduction inhibitor containing an extract from *Justicia procumbens*, as an active ingredient.

<1-8> A skin roughness preventive or improver containing an extract from *Justicia procumbens*, as an active ingredient.

<1-9> The transglutaminase activator, the ceramide production enhancer, the epidermal cornification improver, the skin moisturizing function improver, the skin barrier function improver, the horny cell layer moisture content increasing agent, the horny cell layer moisture content reduction inhibitor, or the skin roughness preventive or improver described in any one of the above items <1-1> to <1-8>, wherein the extract from *Justicia procumbens* is an extract from an entire plant of *Justicia procumbens*.

<1-10> The transglutaminase activator, the ceramide production enhancer, the epidermal cornification improver, the skin moisturizing function improver, the skin barrier function improver, the horny cell layer moisture content increasing agent, the horny cell layer moisture content reduction inhibitor, or the skin roughness preventive or improver described in any one of the above items <1-1> to <1-9>, wherein the extract from *Justicia procumbens* is obtained by extracting *Justicia procumbens* using, as an extraction solvent, an ethanol aqueous solution (preferably an ethanol aqueous solution having an alcohol content of 30 vol % or more, more preferably of 40 vol % or more).

<1-11> The transglutaminase activator, the ceramide production enhancer, the epidermal cornification improver, the skin moisturizing function improver, the skin barrier function improver, the horny cell layer moisture content increasing agent, the horny cell layer moisture content reduction inhibitor, or the skin roughness preventive or improver described in any one of the above items <1-1> to <1-10>, wherein the content of the active ingredient is 0.00001 mass % or more (preferably 0.0001 mass % or more, and more preferably 0.0005 mass % or more) and 20 mass % or less (preferably 10 mass % or less, and more preferably 5 mass % or less).

<1-12> Use of an extract from *Justicia procumbens*, as a transglutaminase activator or a ceramide production enhancer.

<1-13> Use of an extract from *Justicia procumbens*, in the manufacture of a transglutaminase activator or a ceramide production enhancer.

<1-14> A method of using an extract from *Justicia procumbens*, as a transglutaminase activator or a ceramide production enhancer.

<1-15> A method of activating transglutaminase or a method of enhancing ceramide production, using an extract from *Justicia procumbens*.

<1-16> The method described in the above item <1-15>, wherein the extract is applied to a subject who desires prevention or treatment of epidermal incomplete cornification, improvement of a skin moisturizing or skin barrier function, or prevention or improvement of skin roughness.

<1-17> The method described in the above item <1-15> or <1-16>, wherein the extract is applied under conditions needing application of the extract (preferably under conditions of low humidity and dryness).

<1-18> The method described in any one of the above items <1-15> to <1-17>, wherein the extract is administered to a skin.

<1-19> The use or method described in any one of the above items <1-12> to <1-18>, wherein the extract from *Justicia procumbens* is an extract from an entire plant of *Justicia procumbens*.

<1-20> The use or method described in any one of the above items <1-12> to <1-19>, wherein the extract from *Justicia procumbens* is obtained by extracting *Justicia procumbens* using, as an extraction solvent, an ethanol aqueous solution (preferably an ethanol aqueous solution having an alcohol content of 30 vol % or more, more preferably of 40 vol % or more).

<1-21> The use or method described in any one of the above items <1-12> to <1-20>, wherein the content of the extract from *Justicia procumbens* in the transglutaminase activator or the ceramide production enhancer is 0.00001 mass % or more (preferably 0.0001 mass % or more, and more preferably 0.0005 mass % or more) and 20 mass % or less (preferably 10 mass % or less, and more preferably 5 mass % or less).

<1-22> Use of an extract from *Justicia procumbens*, as an epidermal cornification improver, a skin moisturizing function improver, a skin barrier function improver, a horny cell layer moisture content increasing agent, a horny cell layer moisture content reduction inhibitor, or a skin roughness preventive or improver.

<1-23> Use of an extract from *Justicia procumbens*, in the manufacture of an epidermal cornification improver, a skin moisturizing function improver, a skin barrier function improver, a horny cell layer moisture content increasing agent, a horny cell layer moisture content reduction inhibitor, or a skin roughness preventive or improver.

<1-24> A method of using an extract from *Justicia procumbens*, as an epidermal cornification improver, a skin moisturizing function improver, a skin barrier function improver, a horny cell layer moisture content increasing agent, a horny cell layer moisture content reduction inhibitor, or a skin roughness preventive or improver.

<1-25> A method of improving epidermal cornification, a method of improving a skin moisturizing function, a method of improving a skin barrier function, a method of increasing a horny cell layer moisture content, a method of inhibiting horny cell layer moisture content reduction, or a method of preventing or improving skin roughness, containing administering an extract from *Justicia procumbens*.

<1-26> The method described in the above item <1-24> or <1-25>, wherein the extract is applied to a subject who desires prevention or treatment of epidermal incomplete cornification, improvement of a skin moisturizing or skin barrier function, an increase in a horny cell layer moisture content, inhibition of horny cell layer moisture content reduction, or prevention or improvement of skin roughness.

<1-27> The method described in any one of the above items <1-24> to <1-26>, wherein the extract is applied under conditions needing application of the extract (preferably under conditions of low humidity and dryness).

<1-28> The method described in any one of the above items <1-24> to <1-27>, wherein the extract is administered to a skin.

<1-29> An extract from *Justicia procumbens* for use in the method of preventing or treating the epidermal incomplete cornification of the skin, the method of improving the skin moisturizing function, the method of improving the skin barrier function, the method of increasing the horny cell layer moisture content, the method of inhibiting the horny cell layer moisture content reduction, or the method of preventing or improving the skin roughness.

<1-30> Use of an extract from *Justicia procumbens*, in the manufacture of a drug for preventing or treating epidermal incomplete cornification of a skin, a drug for improving a skin moisturizing function, a drug for improving a skin barrier function, a drug for increasing a horny cell layer moisture content, a drug for inhibiting horny cell layer moisture content reduction, or a drug for preventing or improving skin roughness.

<1-31> Use of an extract from *Justicia procumbens*, for applying to a non-therapeutic method of treating epidermal incomplete cornification of a skin, a skin moisturizing function, a skin barrier function, a horny cell layer moisture content, or skin roughness.

<1-32> The use described in the above item <1-31>, wherein the extract from *Justicia procumbens* is applied in the form of a medical composition or a cosmetic composition.

<1-33> The use described in the above item <1-32>, wherein the extract from *Justicia procumbens* is applied in the form of an external application composition.

<1-34> The use described in the above item <1-31>, wherein the extract from *Justicia procumbens* is applied in the form of a food or drink.

<1-35> The use or method described in any one of the above items <1-22> to <1-34>, wherein the extract from *Justicia procumbens* is an extract from an entire plant of *Justicia procumbens*.

<1-36> The use or method described in any one of the above items <1-22> to <1-35>, wherein the extract from *Justicia procumbens* is obtained by extracting *Justicia procumbens* using, as an extraction solvent, an ethanol aqueous solution (preferably an ethanol aqueous solution having an alcohol content of 30 vol % or more, more preferably of 40 vol % or more).

<1-37> The use or method described in any one of the above items <1-22> to <1-36>, wherein the content of the extract from *Justicia procumbens* in the epidermal cornification improver, the skin moisturizing function improver, the skin barrier function improver, the horny cell layer moisture content increasing agent, the horny cell layer moisture content reduction inhibitor, or the skin roughness preventive or improver is 0.00001 mass % or more (preferably 0.0001 mass % or more, and more preferably 0.0005 mass % or more) and 20 mass % or less (preferably 10 mass % or less, and more preferably 5 mass % or less).

<2-1> A transglutaminase activator containing an extract from *Peristrophe japonica*, as an active ingredient.

<2-2> A ceramide production enhancer containing an extract from *Peristrophe japonica*, as an active ingredient.

<2-3> An involucrin expression enhancer containing an extract from *Peristrophe japonica*, as an active ingredient.

<2-4> An epidermal cornification improver containing an extract from *Peristrophe japonica*, as an active ingredient.
<2-5> A skin moisturizing function improver containing an extract from *Peristrophe japonica*, as an active ingredient.
<2-6> A skin barrier function improver containing an extract from *Peristrophe japonica*, as an active ingredient
<2-7> A skin roughness preventive or improver containing an extract from *Peristrophe japonica*, as an active ingredient.
<2-8> A wavy hair former containing an extract from *Peristrophe japonica*, as an active ingredient.
<2-9> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <2-1> to <2-8>, wherein the extract from *Peristrophe japonica* is an extract from an entire plant of *Peristrophe japonica*.
<2-10> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <2-1> to <2-9>, wherein the extract from *Peristrophe japonica* is obtained by extracting *Peristrophe japonica* using, as an extraction solvent, an ethanol aqueous solution (preferably an ethanol aqueous solution having an alcohol content of 30 vol % or more, more preferably of 40 vol % or more).
<2-11> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <2-1> to <2-10>, wherein the content of the active ingredient is 0.00001 mass % or more (preferably 0.0001 mass % or more, and more preferably 0.0005 mass % or more) and 20 mass % or less (preferably 10 mass % or less, and more preferably 5 mass % or less).
<2-12> Use of an extract from *Peristrophe japonica*, as a transglutaminase activator, a ceramide production enhancer, or an involucrin expression enhancer.
<2-13> Use of an extract from *Peristrophe japonica*, in the manufacture of a transglutaminase activator, a ceramide production enhancer, or an involucrin expression enhancer.
<2-14> A method of using an extract from *Peristrophe japonica*, as a transglutaminase activator, a ceramide production enhancer, or an involucrin expression enhancer.
<2-15> A method of activating transglutaminase, a method of enhancing ceramide production, or a method of enhancing involucrin expression, using an extract from *Peristrophe japonica*.
<2-16> The method described in the above item <2-15>, wherein the extract is applied to a subject who desires prevention or treatment of epidermal incomplete cornification, improvement of a skin moisturizing or skin barrier function, prevention or improvement of skin roughness, or wavy hair formation.
<2-17> The method described in the above item <2-15> or <2-16>, wherein the extract is applied under conditions needing application of the extract (preferably under conditions of low humidity and dryness).
<2-18> The method described in any one of the above items <2-15> to <2-17>, wherein the extract is administered to a skin, a scalp or hair.
<2-19> The use or method described in any one of the above items <2-12> to <2-18>, wherein the extract from *Peristrophe japonica* is an extract from an entire plant of *Peristrophe japonica*.
<2-20> The use or method described in any one of the above items <2-12> to <2-19>, wherein the extract from *Peristrophe japonica* is obtained by extracting *Peristrophe japonica* using, as an extraction solvent, an ethanol aqueous solution (preferably an ethanol aqueous solution having an alcohol content of 30 vol % or more, more preferably of 40 vol % or more).
<2-21> The use or method described in any one of the above items <2-12> to <2-20>, wherein the content of the extract from *Peristrophe japonica* in the transglutaminase activator, the ceramide production enhancer, or the involucrin expression enhancer is 0.00001 mass % or more (preferably 0.0001 mass % or more, and more preferably 0.0005 mass % or more) and 20 mass % or less (preferably 10 mass % or less, and more preferably 5 mass % or less).
<2-22> Use of an extract from *Peristrophe japonica*, as an epidermal cornification improver, a skin moisturizing function improver, a skin barrier function improver, a skin roughness preventive or improver, or a wavy hair former.
<2-23> Use of an extract from *Peristrophe japonica*, in the manufacture of an epidermal cornification improver, a skin moisturizing function improver, a skin barrier function improver, a skin roughness preventive or improver, or a wavy hair former.
<2-24> A method of using an extract from *Peristrophe japonica*, as an epidermal cornification improver, a skin moisturizing function improver, a skin barrier function improver, a skin roughness preventive or improver, or a wavy hair former.
<2-25> A method of improving epidermal cornification, a method of improving a skin moisturizing function, a method of improving a skin barrier function, a method of preventing or improving skin roughness, or a method of forming wavy hair, containing administering an extract from *Peristrophe japonica*.
<2-26> The method described in the above item <2-24> or <2-25>, wherein the extract is applied to a subject who desires prevention or treatment of epidermal incomplete cornification, improvement of a skin moisturizing or skin barrier function, prevention or improvement of skin roughness, or wavy hair formation.
<2-27> The method described in any one of the above items <2-24> to <2-26>, wherein the extract is applied under conditions needing application of the extract (preferably under conditions of low humidity and dryness).
<2-28> The method described in any one of the above items <2-24> to <2-27>, wherein the extract is administered to a skin, a scalp or hair.
<2-29> An extract from *Peristrophe japonica* for use in the method of preventing or treating the epidermal incomplete cornification of the skin, the method of improving the skin moisturizing function, the method of improving the skin barrier function, the method of preventing or improving the skin roughness, or the method of forming wavy hair.
<2-30> Use of an extract from *Peristrophe japonica*, in the manufacture of a drug for preventing or treating epidermal incomplete cornification of a skin, a drug for improving a skin moisturizing function, a drug for improving a skin barrier function, a drug for preventing or improving skin roughness, or a drug for forming wavy hair.
<2-31> Use of an extract from *Peristrophe japonica*, for applying to a non-therapeutic method of treating epidermal incomplete cornification of a skin, a skin moisturizing function, a skin barrier function, skin roughness, or wavy hair formation.

<2-32> The use described in the above item <2-31>, wherein the extract from *Peristrophe japonica* is applied in the form of a medical composition or a cosmetic composition.

<2-33> The use described in the above item <2-32>, wherein the extract from *Peristrophe japonica* is applied in the form of an external application composition.

<2-34> The use described in the above item <2-31>, wherein the extract from *Peristrophe japonica* is applied in the form of a food or drink.

<2-35> The use or method described in any one of the above items <2-22> to <2-34>, wherein the extract from *Peristrophe japonica* is an extract from an entire plant of *Peristrophe japonica*.

<2-36> The use or method described in any one of the above items <2-22> to <2-35>, wherein the extract from *Peristrophe japonica* is obtained by extracting *Peristrophe japonica* using, as an extraction solvent, an ethanol aqueous solution (preferably an ethanol aqueous solution having an alcohol content of 30 vol % or more, more preferably of 40 vol % or more).

<2-37> The use or method described in any one of the above items <2-22> to <2-36>, wherein the content of the extract from *Peristrophe japonica* in the epidermal cornification improver, the skin moisturizing function improver, the skin barrier function improver, the skin roughness preventive or improver, or the wavy hair former is 0.00001 mass % or more (preferably 0.0001 mass % or more, and more preferably 0.0005 mass % or more) and 20 mass % or less (preferably 10 mass % or less, and more preferably 5 mass % or less).

<3-1> A transglutaminase activator containing at least one kind of compound represented by Formula (1), as an active ingredient.

<3-2> A ceramide production enhancer containing at least one kind of compound represented by Formula (1), as an active ingredient.

<3-3> An involucrin expression enhancer containing at least one kind of compound represented by Formula (1), as an active ingredient.

<3-4> An epidermal cornification improver containing at least one kind of compound represented by Formula (1), as an active ingredient.

<3-5> A skin moisturizing function improver containing at least one kind of compound represented by Formula (1), as an active ingredient.

<3-6> A skin barrier function improver containing at least one kind of compound represented by Formula (1), as an active ingredient.

<3-7> A skin roughness preventive or improver containing at least one kind of compound represented by Formula (1), as an active ingredient.

<3-8> A wavy hair former containing at least one kind of compound represented by Formula (1), as an active ingredient.

<3-9> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <3-1> to <3-8>, wherein, in Formula (1), $R_1$ and $R_2$ each are a hydrogen atom, or a linear or branched alkoxy group having 1 to 4 carbon atoms (preferably a hydrogen atom or an alkoxy group having 1 or 2 carbon atoms, more preferably a hydrogen atom or a methoxy group); and $R_3$ is a hydrogen atom.

<3-10> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <3-1> to <3-8>, wherein, in Formula (1), $R_1$ is a hydrogen atom; and $R_2$ and $R_3$ are bonded with each other to form a methylenedioxy group.

<3-11> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <3-1> to <3-10>, wherein, in Formula (1), $R_4$ and $R_5$ are bonded with each other to form a methylenedioxy group.

<3-12> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <3-1> to <3-10>, wherein, in Formula (1), $R_4$, $R_5$ and $R_6$ are a hydrogen atom.

<3-13> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <3-1> to <3-12>, wherein the compound represented by Formula (1) is a compound represented by Formula (11) or a compound represented by any one of Formulas (2) to (4).

<3-14> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <3-1> to <3-13>, wherein the compound represented by Formula (1) is selected from the group consisting of the following compounds (11) to (19).

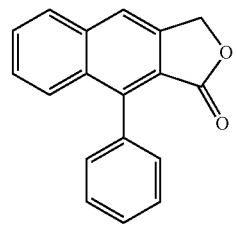

(11)

-continued

(12) 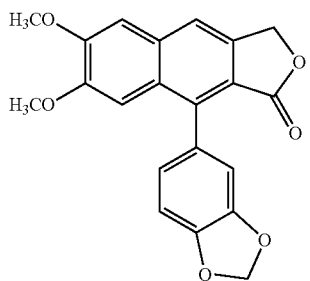

(13) 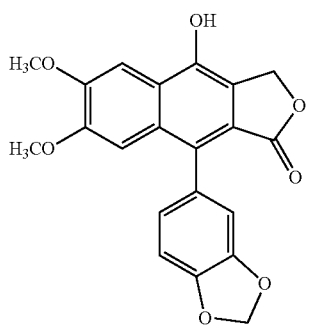

(14) 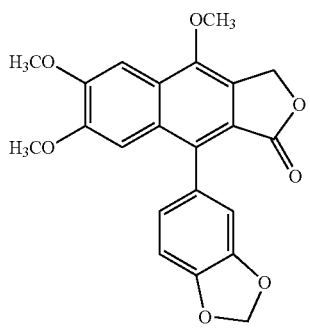

(15) 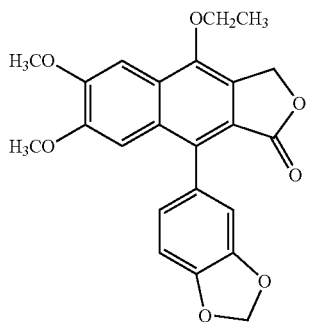

(16) 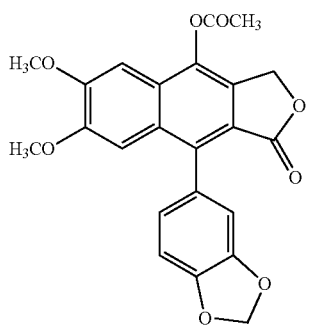

-continued

(17) 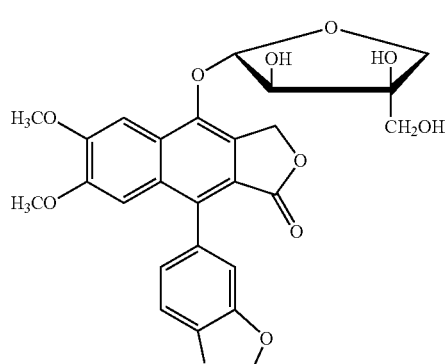

(18) 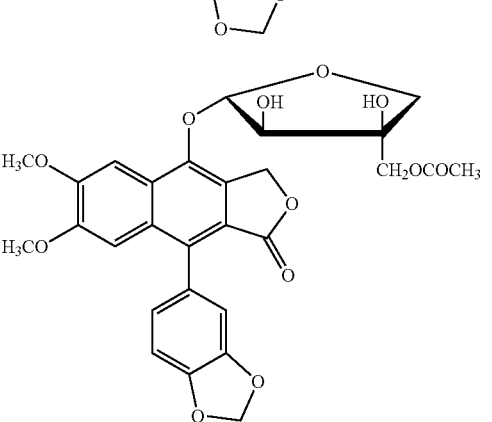

(19) 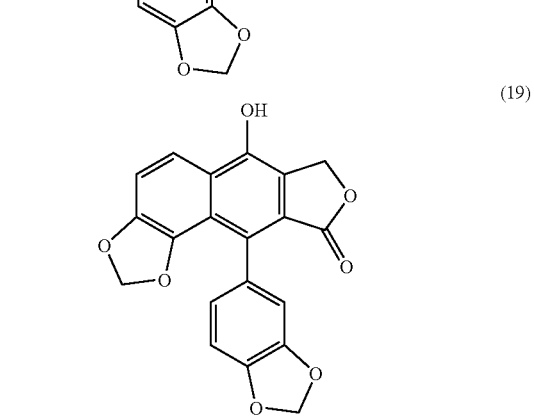

<3-15> The transglutaminase activator, the ceramide production enhancer, the involucrin expression enhancer, the epidermal cornification improver, the skin moisturizing function improver, the skin barrier function improver, the skin roughness preventive or improver, or the wavy hair former described in any one of the above items <3-1> to <3-14>, wherein the content of the active ingredient is $1.0 \times 10^{-10}$ mass % or more (preferably $1.0 \times 10^{-9}$ mass % or more, and more preferably $1.0 \times 10^{-8}$ mass % or more) and 0.01 mass % or less (preferably 0.005 mass % or less, more preferably 0.001 mass % or less, and further preferably $1.0 \times 10^{-4}$ mass % or less).

<3-16> Use of at least one kind of compound represented by Formula (1), as a transglutaminase activator, a ceramide production enhancer or an involucrin expression enhancer.

<3-17> Use of at least one kind of compound represented by Formula (1), in the manufacture of a transglutaminase activator, a ceramide production enhancer, or an involucrin expression enhancer.

<3-18> A method of using at least one kind of compound represented by Formula (1), as a transglutaminase activator, a ceramide production enhancer, or an involucrin expression enhancer.

<3-19> A method of activating transglutaminase, a method of enhancing ceramide production, or a method of enhancing involucrin expression, using at least one kind of compound represented by Formula (1).

<3-20> The method described in the above item <3-19>, wherein the compound is applied to a subject who desires prevention or treatment of epidermal incomplete cornification, improvement of a skin moisturizing or skin barrier function, prevention or improvement of skin roughness, or wavy hair formation.

<3-21> The method described in the above item <3-19> or <3-20>, wherein the compound is applied under conditions needing application of the compound (preferably under conditions of low humidity and dryness).

<3-22> The method described in any one of the above items <3-19> to <3-21>, wherein the compound is administered to a skin, a scalp or hair.

<3-23> The use or method described in any one of the above items <3-16> to <3-22>, wherein, in Formula (1), $R_1$ and $R_2$ each are a hydrogen atom, or a linear or branched alkoxy group having 1 to 4 carbon atoms (preferably a hydrogen atom or an alkoxy group having 1 or 2 carbon atoms, more preferably a hydrogen atom or a methoxy group); and $R_3$ is a hydrogen atom.

<3-24> The use or method described in any one of the above items <3-16> to <3-22>, wherein, in Formula (1), $R_1$ is a hydrogen atom; and $R_2$ and $R_3$ are bonded with each other to form a methylenedioxy group.

<3-25> The use or method described in any one of the above items <3-16> to <3-24>, wherein, in Formula (1), $R_4$ and $R_5$ are bonded with each other to form a methylenedioxy group.

<3-26> The use or method described in any one of the above items <3-16> to <3-24>, wherein, in Formula (1), $R_4$, $R_5$ and $R_6$ are a hydrogen atom.

<3-27> The use or method described in any one of the above items <3-16> to <3-26>, wherein the compound represented by Formula (1) is a compound represented by Formula (11) or a compound represented by any one of Formulas (2) to (4).

<3-28> The use or method described in any one of the above items <3-16> to <3-27>, wherein the compound represented by Formula (1) is selected from the group consisting of the compounds (11) to (19).

<3-29> The use or method described in any one of the above items <3-16> to <3-28>, wherein the content of the at least one kind of compound represented by Formula (1) in the transglutaminase activator, the ceramide production enhancer, or the involucrin expression enhancer is $1.0 \times 10^{-19}$ mass % or more (preferably $1.0 \times 10^{-9}$ mass % or more, and more preferably $1.0 \times 10^{-8}$ mass % or more) and 0.01 mass % or less (preferably 0.005 mass % or less, more preferably 0.001 mass % or less, and further preferably $1.0 \times 10^{-4}$ mass % or less).

<3-30> Use of at least one kind of compound represented by Formula (1), as an epidermal cornification improver, a skin moisturizing function improver, a skin barrier function improver, a skin roughness preventive or improver, or a wavy hair former.

<3-31> Use of at least one kind of compound represented by Formula (1), in the manufacture of an epidermal cornification improver, a skin moisturizing function improver, a skin barrier function improver, a skin roughness preventive or improver, or a wavy hair former.

<3-32> A method of using at least one kind of compound represented by Formula (1), as an epidermal cornification improver, a skin moisturizing function improver, a skin barrier function improver, a skin roughness preventive or improver, or a wavy hair former.

<3-33> A method of improving epidermal cornification, a method of improving a skin moisturizing function, a method of improving a skin barrier function, a method of preventing or improving skin roughness, or a method of forming wavy hair, containing administering at least one kind of compound represented by Formula (1).

<3-34> The method described in the above item <3-32> or <3-33>, wherein the compound is applied to a subject who desires prevention or treatment of epidermal incomplete cornification, improvement of a skin moisturizing or skin barrier function, prevention or improvement of skin roughness, or wavy hair formation.

<3-35> The method described in any one of the above items <3-32> to <3-34>, wherein the compound is applied under conditions needing application of the compound (preferably under conditions of low humidity and dryness).

<3-36> The method described in any one of the above items <3-32> to <3-35>, wherein the compound is administered to a skin, a scalp or hair.

<3-37> At least one kind of compound represented by Formula (1) for use in the method of preventing or treating the epidermal incomplete cornification of a skin, the method of improving a skin moisturizing function, the method of improving a skin barrier function, the method of preventing or improving skin roughness, or the method of forming wavy hair.

<3-38> Use of at least one kind of compound represented by Formula (1), in the manufacture of a drug for preventing or treating epidermal incomplete cornification of a skin, a drug for improving a skin moisturizing function, a drug for improving a skin barrier function, a drug for preventing or improving skin roughness, or a drug for forming wavy hair.

<3-39> Use of at least one kind of compound represented by Formula (1), for applying to a non-therapeutic method of treating epidermal incomplete cornification of a skin, a skin moisturizing function, a skin barrier function, skin roughness, or wavy hair formation.

<3-40> The use described in the above item <3-39>, wherein the at least one kind of compound represented by Formula (1) is applied in the form of a medical composition or a cosmetic composition.

<3-41> The use described in the above item <3-40>, wherein the at least one kind of compound represented by Formula (1) is applied in the form of an external application composition.

<3-42> The use described in the above item <3-39>, wherein the at least one kind of compound represented by Formula (1) is applied in the form of a food or drink.

<3-43> The use or method described in any one of the above items <3-30> to <3-42>, wherein, in Formula (1), $R_1$ and $R_2$ each are a hydrogen atom, or a linear or branched alkoxy group having 1 to 4 carbon atoms (preferably a hydrogen atom or an alkoxy group having 1 or 2 carbon atoms, more preferably a hydrogen atom or a methoxy group); and $R_3$ is a hydrogen atom.

<3-44> The use or method described in any one of the above items <3-30> to <3-42>, wherein, in Formula (1), $R_1$ is a hydrogen atom; and $R_2$ and $R_3$ are bonded with each other to form a methylenedioxy group.

<3-45> The use or method described in any one of the above items <3-30> to <3-44>, wherein, in Formula (1), $R_4$ and $R_5$ are bonded with each other to form a methylenedioxy group.

<3-46> The use or method described in any one of the above items <3-30> to <3-44>, wherein, in Formula (1), $R_4$, $R_5$ and $R_6$ are a hydrogen atom.

<3-47> The use or method described in any one of the above items <3-30> to <3-46>, wherein the compound represented by Formula (1) is a compound represented by Formula (11) or a compound represented by any one of Formulas (2) to (4).

<3-48> The use or method described in any one of the above items <3-30> to <3-47>, wherein the compound represented by Formula (1) is selected from the group consisting of the compounds (11) to (19).

<3-49> The use or method described in any one of the above items <3-30> to <3-48>, wherein the content of the at least one kind of compound represented by Formula (1) in the epidermal cornification improver, the skin moisturizing function improver, the skin barrier function improver, the skin roughness preventive or improver, or the wavy hair former is $1.0 \times 10^{-10}$ mass % or more (preferably $1.0 \times 10^{-9}$ mass % or more, and more preferably $1.0 \times 10^{-8}$ mass % or more) and 0.01 mass % or less (preferably 0.005 mass % or less, more preferably 0.001 mass % or less, and further preferably $1.0 \times 10^{-4}$ mass % or less).

EXAMPLES

Hereinafter, the present invention will be described more in detail with reference to Examples, but the present invention is not limited thereto.

Preparation Example 1-1

800 mL of an aqueous 50 vol % ethanol aqueous solution was added to 80 g of entire plant of *Justicia procumbens* (available from SHINWA BUSSAN CO., LTD.), which was extracted with the solution at a room temperature for 7 days. Then, the resultant material was filtered to obtain a crude extract, and then the crude extraction was subjected to concentration to dryness to obtain 6.6 g of an extracted solid content. This extracted solid content was dissolved into a 50 vol % ethanol aqueous solution to be 1.0% (w/v) in a residue on evaporation to prepare a 50 vol % ethanol extract of *Justicia procumbens*.

Preparation Example 1-2

500 mL of an aqueous 95 vol % ethanol solution was added to 50 g of entire plant of *Justicia procumbens* (available from SHINWA BUSSAN CO., LTD.), which was extracted with the solution at a room temperature for 7 days. Then, the resultant material was filtered to obtain a crude extract, and then the crude extraction was subjected to concentration to dryness to obtain 897 mg of an extracted solid content. This extracted solid content was dissolved into a 95 vol % ethanol aqueous solution to be 1.0% (w/v) in a residue on evaporation to prepare a 95 vol % ethanol extract of *Justicia procumbens*.

Preparation Example 2-1

10 g of entire plant of *Peristrophe japonica* (available from SHINWA BUSSAN CO., LTD.) finely was cut, and 100 mL of an aqueous 30 vol % ethanol solution was added thereto. Then, extraction was carried out for 7 days under the conditions of standing at room temperature. Thereafter, the extract was filtered to obtain 61 mL of an extract from *Peristrophe japonica*. For the extract thus obtained, the evaporation residue was calculated, and the evaporation residue was found to be 1.10% (w/v). This residue was diluted with a 30 vol % ethanol aqueous solution to prepare a 1.0% (w/v) (extract solid content) extract.

<Calculation of Evaporation Residue>

1 mL of the extract from *Peristrophe japonica* was dried for 6 hours at 105° C. using a dryer (DRY Thermo Unit DTU-1C (trade name) manufactured by TAITEC CORPORATION), and thus, 11.0 mg of a dried product was obtained. The evaporation residue of this extract was calculated by the formula: $11.0/1000 \times 100 = 1.10\%$ (w/v). In the Preparation Examples described below, the evaporation residue of each extract were calculated in the same manner.

Preparation Example 2-2

Extraction was carried using a 50 vol % ethanol aqueous solution under conditions similar to the conditions in Preparation Example 2-1. Thereafter, the extraction was filtered to obtain 58 mL of an extract from *Peristrophe japonica*. For the extract thus obtained, the evaporation residue was calculated, and the evaporation residue was found to be 0.92% (w/v). This extract was concentrated, and then a 1.0% (w/v) (extract solid content) extract was prepared with a 50 vol % ethanol aqueous solution.

Preparation Example 2-3

Extraction was carried using a 60 vol % ethanol aqueous solution under conditions similar to the conditions in Preparation Example 2-1. Thereafter, the extraction was filtered to obtain 58 mL of an extract from *Peristrophe japonica*. For the extract thus obtained, the evaporation residue was calculated, and the evaporation residue was found to be 0.79% (w/v). This extract was concentrated, and then a 1.0% (w/v) (extract solid content) extract was prepared with a 60 vol % ethanol aqueous solution.

Preparation Example 2-4

Extraction was carried using a 70 vol % ethanol aqueous solution under conditions similar to the conditions in Preparation Example 2-1. Thereafter, the extraction was filtered to obtain 60 mL of an extract from *Peristrophe japonica*. For the extract thus obtained, the evaporation residue was calculated, and the evaporation residue was found to be 0.70% (w/v). This extract was concentrated, and then a 1.0% (w/v) (extract solid content) extract was prepared with a 70 vol % ethanol aqueous solution.

Preparation Example 2-5

Extraction was carried using a 80 vol % ethanol aqueous solution under conditions similar to the conditions in Preparation Example 2-1. Thereafter, the extraction was filtered to obtain 55 mL of an extract from *Peristrophe japonica*. For the extract thus obtained, the evaporation residue was calculated, and the evaporation residue was found to be 0.60% (w/v). This extract was concentrated, and then a 1.0% (w/v) (extract solid content) extract was prepared with a 80 vol % ethanol aqueous solution.

Preparation Example 2-6

Extraction was carried using a 90 vol % ethanol aqueous solution under conditions similar to the conditions in Preparation Example 2-1. Thereafter, the extraction was filtered to obtain 53 mL of an extract from *Peristrophe japonica*. For the extract thus obtained, the evaporation residue was calculated, and the evaporation residue was found to be 0.36% (w/v). This extract was concentrated and dried, and then a 1.0% (w/v) (extract solid content) extract was prepared with a 90 vol % ethanol aqueous solution.

Preparation Example 2-7

Extraction was carried using a 99.5 vol % ethanol aqueous solution under conditions similar to the conditions in Preparation Example 2-1. Thereafter, the extraction was filtered to obtain 52 mL of an extract from *Peristrophe japonica*. For the extract thus obtained, the evaporation residue was calculated, and the evaporation residue was found to be 0.17% (w/v). This extract was concentrated and dried, and then a 1.0% (w/v) (extract solid content) extract was prepared with a 99.5 vol % ethanol aqueous solution.

Preparation Example 2-8

600 g of entire plant of *Peristrophe japonica* (available from SHINWA BUSSAN CO., LTD.) finely was cut, and 6,000 mL of an aqueous 99.5 vol % ethanol solution was added thereto. Then, extraction was carried out for 7 days under the conditions of standing at room temperature. Thereafter, the extraction was filtered to obtain 4,504 mL of an extract from *Peristrophe japonica*. To 4,000 mL of the resultant extract, 2,000 mL of hexane was added, and the resultant mixture was stirred, and then 6,000 mL of water was further added thereto. The resultant mixture was subjected to liquid-liquid distribution, and then 8,367 mL of a lower layer was taken out. To 2,500 mL of the resultant extract, 1,000 mL of 1,3-butylene glycol was added, and subjected to concentration by means of an evaporator to remove ethanol and water. After 1,500 mL of water was added thereto, sedimentation was carried out under conditions of 5° C. and 4 days. An insoluble matter was removed by filtration, and then a 40 vol % 1,3-butylene glycol aqueous solution was added to 2,403 mL of the resultant filtrate to prepare 3,266 mL of an extract. For the extract thus obtained, the evaporation residue was calculated, and the evaporation residue was found to be 0.02% (w/v).

Production Example 3-1 Preparation of Compound Represented by Formula (1)

*Justicia procumbens* (available from SHINWA BUSSAN CO., LTD.) 500 g was extracted with 5 L of 50 vol % ethanol, and the solvent was concentrated. Thus, 44 g of an extracted solid fraction was obtained. The obtained extracted solid fraction was subjected to a liquid-liquid distribution using water and ethyl acetate, to obtain the ethyl acetate layer of 4.7 g (yield 11%).

The ethyl acetate layer was further fractionated by silica gel column chromatography. As the silica gel column, Hi-Flush Column (4 L, manufactured by Yamazen Corporation) was used. Elution was carried out by flowing, first, 100% hexane for 10 minutes, and then applying a gradient from 0% to 100% in an ethyl acetate ratio using hexane-ethyl acetate over 60 minutes, and then applying a gradient from 0% to 10% in a methanol ratio using ethyl acetate-methanol over 30 minutes, and finally using 100% methanol for 30 minutes. After flowing was carried out at a flow rate of 30 mL/min to carry out fractionation every 2 minutes, and then fractions having close Rf values were collected by TLC analysis of each fraction, respectively, to obtain seven fractions.

With regard to the fraction (4) (0.8 g, yield: 1.8%), a precipitate caused by addition of methanol was further fractionated by HPLC. When Inertsil ODS-3 (14×250 mm, manufactured by GL Sciences Inc.) was used as a column, and elution was carried out at a flow rate of 15 mL/min at a detection wavelength of 254 nm, and using a 0.1% formic acid aqueous solution-acetonitrile at 50% in an acetonitrile ratio for 20 minutes, two main peaks were obtained. A fraction at each peak was fractionated, and taken as a fraction (8) and a fraction (9). Transglutaminase activity was confirmed to exist in both the fraction (8) (48 mg, yield: 0.38%) and the fraction (9) (58 mg, yield: 0.46%).

With regard to a fraction (7) (1.91 g, yield: 4.3%), 470 mg from the fraction was used, and further fractionated by HPLC. Inertsil ODS-3 (10×250 mm, manufactured by GL Sciences Inc.) was used as a column, elution was carried out at a flow rate of 7.5 mL/min, at a detection wavelength of 254 nm, using a 0.1% formic acid aqueous solution-acetonitrile at 35% in an acetonitrile ratio for 20 minutes. The fraction was further fractionated into a fraction (10), a fraction (11) and a fraction (12) according to peaks, and transglutaminase activity was confirmed to exist in the fraction (11) (14.1 mg, yield: 0.13%).

The fractions (8), (9) and (11) each were subjected to a structure analysis using NMR. As a result, as shown in the tables, the fraction (8) was identified as the exemplified compound (12), the fraction (9) was identified as the exemplified compound (14), and the fraction (11) was identified as the exemplified compound (17).

TABLE 1

Fraction (8) (Measurement solvent: Deuterated chloroform)

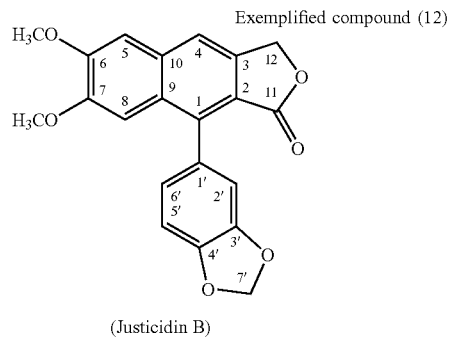

(Justicidin B)

|  | 13C | | 1H | |
| --- | --- | --- | --- | --- |
|  | Isolated Component | Value described in Literature | Isolated Component | Value described in Literature |
| 1 | 139.4 | 139.7 |  |  |
| 2 | 118.4 | 118.6 |  |  |
| 3 | 139.5 | 139.7 |  |  |
| 4 | 118.2 | 118.5 | 7.71 | 7.71 |
| 5 | 105.9 | 106.1 | 7.19 | 7.19 |
| 6 | 151.7 | 151.9 |  |  |
| 7 | 149.9 | 150.2 |  |  |
| 8 | 105.7 | 105.9 | 7.11 | 7.12 |
| 9 | 128.7 | 129 |  |  |
| 10 | 133.1 | 133.3 |  |  |
| 11 | 169.9 | 169.9 |  |  |
| 12 | 68 | 68.2 | 5.38 | 5.39 |
| 1' | 128.3 | 128.5 |  |  |
| 2' | 110.5 | 110.7 | 6.86 | 6.86 |
| 3' | 147.5 | 147 |  |  |
| 4' | 147.4 | 147 |  |  |
| 5' | 108.1 | 108.4 | 6.97 | 6.98 |
| 6' | 123.4 | 123.6 | 6.84 | 6.84 |

TABLE 1-continued

Fraction (8) (Measurement solvent: Deuterated chloroform)

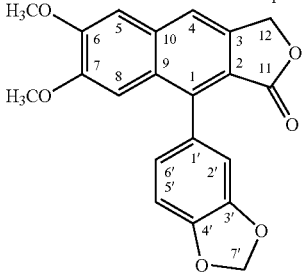

Exemplified compound (12)

(Justicidin B)

|  | 13C | | 1H | |
| --- | --- | --- | --- | --- |
|  | Isolated Component | Value described in Literature | Isolated Component | Value described in Literature |
| 7' | 101.2 | 101.4 | 6.05, 6.1 | 6.05, 6.1 |
| 6-OMe | 56 | 56.2 | 4.05 | 4.06 |
| 7-OMe | 55.8 | 56 | 3.82 | 3.82 |

Value described in Literature: Tetrahedron, 2002, vol. 58, p. 5989-6001

TABLE 2

Fraction (9) (Measurement solvent: Deuterated chloroform)

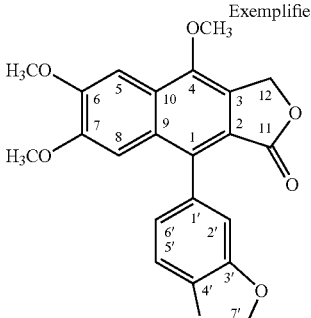

Exemplified compound (14)

(Justicidin A)

|  | 13C | | 1H | |
| --- | --- | --- | --- | --- |
|  | Isolated Component | Value described in Literature | Isolated Component | Value described in Literature |
| 1 | 134.5 | 134.4 | | |
| 2 | 119.4 | 119.3 | | |
| 3 | 124.5 | 124.5 | | |
| 4 | 147.9 | 147.5 | | |
| 5 | 100.7 | 100.6 | 7.54 | 7.55 |
| 6 | 151.7 | 151.6 | | |
| 7 | 150.4 | 150.3 | | |
| 8 | 106.2 | 106.2 | 7.05 | 7.09 |
| 9 | 130.7 | 126 | | |
| 10 | 126 | 130.6 | | |
| 11 | 169.7 | 169.5 | | |
| 12 | 66.8 | 66.6 | 5.54 | 5.55 |
| 1' | 128.6 | 128.5 | | |
| 2' | 110.9 | 110.8 | 6.82 | 6.81 |
| 3' | 147.6 | 147.4 | | |
| 4' | 147.5 | 147.4 | | |
| 5' | 108.3 | 108.1 | 6.95 | 6.95 |
| 6' | 123.7 | 123.6 | 6.79 | 6.77 |
| 7' | 101.3 | 101.2 | 6.04, 6.09 | 6.04, 6.06 |

TABLE 2-continued

Fraction (9) (Measurement solvent: Deuterated chloroform)

Exemplified compound (14)

(Justicidin A)

|  | 13C | | 1H | |
| --- | --- | --- | --- | --- |
|  | Isolated Component | Value described in Literature | Isolated Component | Value described in Literature |
| 4-OMe | 59.8 | 59.6 | 4.13 | 4.12 |
| 6-OMe | 55.9 | 56.3 | 3.8 | 3.8 |
| 7-OMe | 56.3 | 55.9 | 4.07 | 4.08 |

Value described in Literature:
Journal of Natural Products, 1999, vol. 62, p. 1056-1058
Journal of Natural Products, 1986, vol. 49, p. 348-350
Note) In this Table, NMR values of 13C in 9-position and 10-position were reversed in the values of isolated components and the values described in Literature. However, in the isolated components, the values were confirmed by applying INADEQUATE measurement for structural analysis, and therefore the values of the isolated components are thought to be more probable.

TABLE 3

Fraction (11) (Measurement solvent: Deuterated chloroform)

Exemplified compound (17)

Tuberculatin

|  | 13C | | 1H | |
| --- | --- | --- | --- | --- |
|  | Isolated Component | Value described in Literature | Isolated Component | Value described in Literature |
| 1 | 136.9 | 137.1 | | |
| 2 | 120.1 | 126.5 | | |
| 3 | 130.1 | 130.1 | | |
| 4 | 146.4 | 146.4 | | |
| 5 | 102.0 | 101.7 | 7.58 | 7.75 |

TABLE 3-continued

Fraction (11) (Measurement solvent: Deuterated chloroform)

Exemplified compound (17)

Tuberculatin

| | 13C | | 1H | |
|---|---|---|---|---|
| | Isolated Component | Value described in Literature | Isolated Component | Value described in Literature |
| 6 | 153.3 | 153.8 | | |
| 7 | 151.8 | 152.1 | | |
| 8 | 107.1 | 107 | 6.97 | 7.11 |
| 9 | 131.8 | 132 | | |
| 10 | 128.4 | 128.6 | | |
| 11 | 172.3 | 171.8 | | |
| 12 | 68.9 | 68.7 | 5.44 | 5.54 |
| | | | 5.51 | 5.60 |
| 1' | 130.3/130.4 | 130.1 | | |
| 2' | 111.9/112.0 | 111.7 | 6.7 | 6.85 |
| 3' | 149.1 | 149.2 | | |
| 4' | 149.1 | 149.2 | | |
| 5' | 109.07/109.09 | 108.2 | 6.9 | 6.99 |
| 6' | 124.9/125.0 | 124.7 | 6.7 | 6.81 |
| 7' | 102.7 | 102.4 | 6.0 | 6.07 |
| | | | | 6.02 | 6.09 |
| 6-OMe | 56.6 | 56.2 | 3.960/3.965 | 4.06 |
| 7-OMe | 56.1 | 55.7 | 3.679/3.682 | 3.77 |
| 1" | 112.97/113.0 | 112.9 | 5.45 | 5.57 |
| 2" | 78.8 | 78.5 | 4.49 | 4.56 |
| 3" | 80.4 | 79.5 | | |
| 4" | 76.1 | 75.7 | 3.9 | 3.97 |
| | | | 4.31 | 4.38 |
| 5" | 64.3 | 64.2 | 3.66 | 3.71 |

Value described in Literature: Chemical & Pharmaceutical Bulletin, 2002, vol. 50, p. 844-846

Production Example 3-2 Preparation of Compound Represented by Formula (1)

*Justicia procumbens* (available from SHINWA BUSSAN CO., LTD.) 500 g was extracted with 5 L of 99.5 vol % ethanol, and the solvent was concentrated. Thus, the obtained extracted solid fraction was subjected to a liquid-liquid distribution using water and ethyl acetate, to obtain 3.8 g of the ethyl acetate layer (yield 75.4%).

The ethyl acetate layer in an amount of 2.5 g was further fractionated by silica gel column chromatography. As the silica gel column, Hi-Flush Column (2 L, manufactured by Yamazen Corporation) was used. Elution was carried out by flowing, first, 100% hexane for 10 minutes, and then applying a gradient from 0% to 100% in an ethyl acetate ratio using hexane-ethyl acetate over 60 minutes, and then applying a gradient from 0% to 10% in a methanol ratio using ethyl acetate-methanol over 30 minutes, and finally using 100% methanol for 30 minutes. After flowing was carried out at a flow rate of 6 mL/min to carry out fractionation every 2 minutes, and then fractions having close Rf values were collected by TLC analysis of each fraction, respectively, to obtain fractions (13), (14) and (15).

With regard to the fraction (14) (325.3 mg, yield: 9.8%), 300 mg from the fraction was used, and further fractionated by HPLC. Inertsil ODS-3 (10×250 mm, manufactured by GL Sciences Inc.) was used as a column, elution was carried out at a flow rate of 7.5 mL/min, at a detection wavelength of 254 nm, using a 0.1% formic acid aqueous solution-acetonitrile at 30% in an acetonitrile ratio for 30 minutes, at 38% in an acetonitrile ratio for 20 minutes and at 100% in an acetonitrile ratio for 20 minutes. The fraction was further fractionated into a fraction (16), a fraction (17) and a fraction (18) according to peaks.

The fraction (17) (13.10 mg, yield: 0.4%) was further fractionated by HPLC. Inertsil ODS-3 (10×250 mm, manufactured by GL Sciences Inc.) was used as a column, elution was carried out at a flow rate of 7.5 mL/min, at a detection wavelength of 254 nm, using a 0.1% formic acid aqueous solution-methanol at 55% in an methanol ratio for 45 minutes. The fraction was further fractionated into a fraction (19), a fraction (20) and a fraction (21) according to peaks, and transglutaminase activity was confirmed to exist in the fraction (20) (10.3 mg, yield: 0.3%).

The fraction (20) was subjected to a structure analysis using NMR. As a result, as shown in the table, the fraction (20) was identified as the exemplified compound (18).

TABLE 4

Exemplified compound (18)

(Tuberculatin-5"-acetate)

| | 13C | | 1H | |
|---|---|---|---|---|
| | Isolated Component (In CDCl$_3$) | Isolated Component (In CDCl$_3$) | Isolated Component (In DMSO-d6) | Value described in Literature *1 (In DMSO-d6) |
| 1 | 136.2 | | | |
| 2 | 118.3 | | | |
| 3 | 129.0 | | | |
| 4 | 144.7 | | | |
| 5 | 100.4 | 7.58 | 7.64 | 7.62 |
| 6 | 152.0 | | | |
| 7 | 150.4 | | | |
| 8 | 100.4 | 7.06 | 7.00 | 6.98 |
| 9 | 126.8 | | | |
| 10 | 130.8 | | | |
| 11 | 170.1 | | | |
| 12 | 67.3 | 5.45, 5.52 | 5.50 | 5.48 |
| 1' | 128.4 | | | |
| 2' | 110.7/110.8 | 6.79/6.82 | 6.93 | 6.91 |
| 3' | 147.6 | | | |
| 4' | 147.6 | | | |

TABLE 4-continued

Exemplified compound (18)

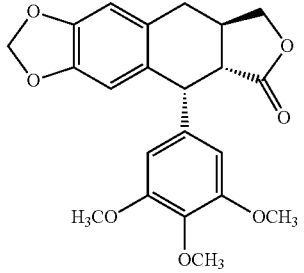

(Tuberculatin-5″-acetate)

| | 13C | 1H | | |
|---|---|---|---|---|
| | Isolated Component (In CDCl$_3$) | Isolated Component (In CDCl$_3$) | Isolated Component (In DMSO-d6) | Value described in Literature *1 (In DMSO-d6) |
| 5' | 108.3 | 6.94/6.95 | 7.05 | 7.03 |
| 6' | 123.7 | 6.77/6.78 | 6.90 | 6.78 |
| 7' | 101.4 | 6.04, 6.08 | 8.13 | 6.11 |
| 1″ | 111.1 | 5.49 | 5.46 | 5.46 |
| 2″ | 78.5 | 4.42 | 4.33 | 4.32 |
| 3″ | 78.0 | | | |
| 4″ | 74.8 | 4.06, 4.27 | 3.87, 4.20 | 3.86, 4.20 |
| 5″ | 66.8 | 4.39 | 4.17 | 4.16 |
| 6″ | 172.0 | | | |
| 7″ | 21.0 | 2.18 | 2.07 | 2.06 |
| 6-OCH$_3$ | 56.2 | 4.06 | 3.97 | 3.95 |
| 7-OCH3 | 66.0 | 3.80 | 3.67 | 3.66 |
| 2″-OH | | | 5.99 | 5.91 |
| 3″-OH | | | 5.28 | 5.22 |

*1 *J. Nat. Prod.*, 1987, vol. 50, p. 748

Production Example 3-3 Preparation of Comparative Compounds

The following comparative compounds (1) and (2) were prepared from an extract from *Thujopsis dolabrata*, in accordance with the method described in Japanese patent No. 4167733.

Comparative compound (1)

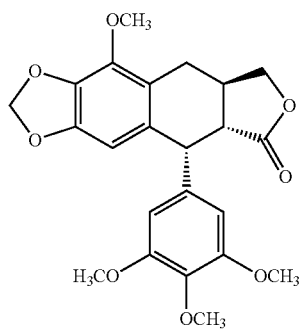

Comparative compound (2)

Test Example 1 Measurement of Transglutaminase Activity

In a 12-well plate, human epidermal keratinocyte lines HEKn (manufactured by Kurabo Industries Ltd.) were seeded in an amount of 4×10$^4$ cells/well, and cultured. As a culture medium, commercially available EpiLife-KG2 manufactured by Kurabo Industries Ltd. was used. Culture was carried out for 1 day under conditions of 37° C. and 5% $CO_2$, and then exchange was carried out for a culture medium containing no growth factor (e.g. BPE, EGH), and then extracts prepared in Production Examples 1-1 and 1-2, and Production Examples 2-1 and 2-8 were added, respectively, such that final concentrations reached values shown in Table 5, or DMSO solutions of various kinds of compounds were added thereto, respectively, such that final concentrations reached values shown in Table 6. Moreover, in place of various kinds of extracts or various kinds of compounds, as controls, a 50 vol % ethanol aqueous solution, a 95 vol % ethanol aqueous solution, or DMSO each being an extraction solvent was added thereto at a final concentration of 0.1% (v/v), respectively, or as a positive control, $CaCl_2$ was added thereto at a final concentration of 1.5 mM, respectively. In addition, an effect of enhancing cornification is known for $CaCl_2$, and $CaCl_2$ was used as the positive control. All of these were further cultured at 37° C. for 3 days.

After completion of culture, a culture liquid was removed, and cells were washed twice with PBS(−), and were collected by means of a cell scraper using 150 μL of extraction buffer solution (10 mM Tris-HCl buffer containing 0.5 mM EDTA, 1% Triton X-100 and Protease inhibitors, pH: 7.4) to obtain a cell crushed liquid by ultrasonication. A supernatant obtained by a centrifugation operation (15,000 rpm, 10 minutes) was used as a lysate for evaluation. Enzyme activity was measured using Transglutaminase Colorimetric Microassay Kit (trade name) according to manufacturer's instructions for use. A protein concentration was quantitatively determined using BCA Protein Assay Kit (trade name, manufactured by Thermo Fisher Scientific, Inc.) according to manufacturer's instructions for use.

The results of evaluation are shown in Table 5 and Table 6. For the extract obtained in Preparation Example 1-1, transglutaminase activity of each extract sample was expressed in terms of a relative value when transglutaminase activity of the control to which the 50 vol % ethanol aqueous solution was added was taken as 1. For the extract obtained in Preparation Example 1-2, the activity was expressed in terms of a relative value when the transglutaminase activity of the control to which the 95 vol % ethanol aqueous solution was added was taken as 1. For extracts obtained in Preparation Examples 2-1 to 2-8, the activity was expressed in terms of relative values when the transglutaminase activity of the control to which the 50 vol % ethanol was added was taken as 1. For various kinds of compounds, the activity was expressed in terms of relative values when the transglutaminase activity of the control to which DMSO was added was taken as 1.

TABLE 5

| Sample | Final concentration of extract | Transglutaminase activity (n = 3) |
|---|---|---|
| Control 1 (50 vol % ethanol) | — | 1.00 ± 0.19 |
| Control 2 (95 vol % ethanol) | — | 1.00 ± 0.40 |
| Positive control ($Ca^{2+}$) | — | 1.51 ± 0.20 |
| Preparation Example 1-1 | 0.001% *1 | 1.36 ± 0.31 |
|  | 0.01% *1 | 1.63 ± 0.49 |
| Preparation Example 1-2 | 0.001% *1 | 2.45 ± 0.38 |
|  | 0.01% *1 | 3.50 ± 1.02 |
| Preparation Example 2-1 | 0.1% *1 | 2.44 ± 0.34 |
|  | 0.01% *1 | 1.47 ± 0.00 |
|  | 0.001% *1 | 1.39 ± 0.05 |
| Preparation Example 2-2 | 0.01% *1 | 2.16 ± 0.47 |
|  | 0.001% *1 | 1.70 ± 0.03 |
| Preparation Example 2-3 | 0.01% *1 | 2.09 ± 0.28 |
| Preparation Example 2-4 | 0.01% *1 | 2.13 ± 0.64 |
| Preparation Example 2-5 | 0.01% *1 | 1.71 ± 0.10 |
| Preparation Example 2-6 | 0.01% *1 | 1.81 ± 1.04 |
| Preparation Example 2-7 | 0.01% *1 | 2.29 ± 0.46 |
| Preparation Example 2-8 | 0.02% *2 | 2.13 ± 0.23 |

*1 Concentration (v/v) of an extract from a solid content of 1%
*2 Concentration (v/v) of an extract from a residue on evaporation of 0.02%

TABLE 6

| Sample | Distribution source | Evaluated Conc. | Transglutaminase activity (n = 3) | Remarks |
|---|---|---|---|---|
| Control 3 (DMSO) | — | — | 1.00 ± 0.19 | Reference |
| Positive control ($Ca^{2+}$) | — | 1.5 mM | 1.51 ± 0.20 | example |
| Exemplified compound (11) | Aldrich | 1 μM | 1.48 ± 0.22 | This invention |
|  |  | 0.1 μM | 1.29 ± 0.40 |  |
|  |  | 0.01 μM | 1.10 ± 0.22 |  |
| Exemplified compound (12) | Production Example 1 | 0.1 μM | 2.80 ± 1.73 |  |
|  |  | 0.01 μM | 1.20 ± 0.16 |  |
| Exemplified compound (13) | Pharmeks LTD | 0.1 μM | 1.75 ± 0.61 |  |
|  |  | 0.01 μM | 1.95 ± 0.53 |  |
| Exemplified compound (14) | Production Example 1 | 1 μM | 2.19 ± 0.98 |  |
|  |  | 0.1 μM | 2.42 ± 0.55 |  |
|  |  | 0.01 μM | 1.22 ± 0.51 |  |
| Exemplified compound (15) | Pharmeks LTD | 1 μM | 1.66 ± 0.33 |  |
|  |  | 0.1 μM | 1.33 ± 0.39 |  |
|  |  | 0.01 μM | 1.25 ± 0.22 |  |
| Exemplified compound (16) | Pharmeks LTD | 1 μM | 2.10 ± 0.86 |  |
|  |  | 0.1 μM | 1.46 ± 0.54 |  |
| Exemplified compound (17) | Production Example 1 | 0.1 μM | 4.39 ± 0.40 |  |
|  |  | 0.01 μM | 1.85 ± 0.81 |  |
| Exemplified compound (18) | Production Example 2 | 1 μM | 5.44 ± 0.19 |  |
|  |  | 0.1 μM | 2.78 ± 0.19 |  |
| Exemplified compound (19) | ChromaDex | 1 μM | 2.37 ± 0.26 |  |
|  |  | 0.1 μM | 1.98 ± 0.83 |  |
| Comparative compound (1) | Production Example 3 | 1 μM | 0.24 ± 0.21 | Comparative example |
| Comparative compound (2) | Production Example 3 | 1 μM | 0.20 ± 0.18 |  |
| Comparative compound (3) | ChromaDex | 1 μM | 0.70 ± 0.24 |  |
|  |  | 0.1 μM | 0.97 ± 0.43 |  |
|  |  | 0.01 μM | 0.75 ± 0.49 |  |
| Comparative compound (4) | ChromaDex | 1 μM | 0.22 ± 0.08 |  |
|  |  | 0.1 μM | 0.39 ± 0.10 |  |
|  |  | 0.01 μM | 0.60 ± 0.28 |  |

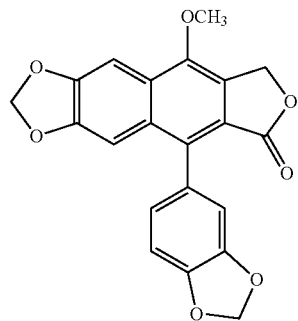

Comparative compound (3)

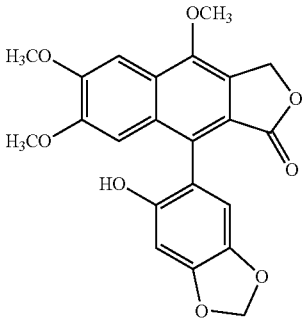

Comparative compound (4)

As shown in Table 5, in systems to which the extract from *Justicia procumbens* or *Peristrophe japonica* was added, the transglutaminase activity was at a level comparable with or higher than the positive control.

Further, as shown in Table 6, no transglutaminase activation effect was found for the comparative compounds (1) to (4). In contrast, in systems to which the compound represented by Formula (1) was added, transglutaminase was activated.

Further, the transglutaminase activity is related to maintenance of a skin barrier function, maintenance or improvement of a moisturizing function, and prevention or improvement of skin roughness. Thus, prevention of epidermal incomplete cornification, improvement of the skin moisturizing function, and prevention or improvement of the skin roughness or the like can be attained by activating the transglutaminase. Accordingly, at least one kind selected from the group consisting of an extract from *Justicia procumbens*, an extract from *Peristrophe japonica*, and a compound represented by Formula (1) having the transglutaminase activation effect can be contained as the active ingredient in the epidermal cornification improver, the skin moisturizing function improver, the skin barrier function improver, and the skin roughness preventive or improver.

Test Example 2-1 Verification of Ceramide Production Enhancing Effect

Normal human epidermal keratinocytes (trade name: NHEK(F), manufactured by Kurabo Industries, Ltd.) were cultured under the conditions of 37° C. and 5% $CO_2$, in a culture medium (trade name: EpiLife-KG2, manufactured by Kurabo Industries, Ltd.) using a culture plate.

Thereafter, the culture medium was exchanged with EpiLife-KG2 without growth factors such as epidermal growth factor, and a dilution prepared from the extract from *Justicia procumbens* prepared in the Preparation Example 1-2, the concentration of which was adjusted to 1 w/v % in terms of solids content, was added to the culture fluid in an amount of 0.01%, 0.05% or 0.1%. Alternatively, the culture medium was exchanged with EpiLife-KG2 without growth factors such as epidermal growth factor, and a dilution prepared from the extract from *Peristrophe japonica* prepared in the Preparation Example 2-2, the concentration of which was adjusted to 1 w/v % in terms of solids content, was added to the culture fluid in an amount of 0.1%. In place of the extract from *Justicia procumbens* or *Peristrophe japonica*, as a control, the 50 vol % ethanol being the extraction solvent was added at the final concentration of 0.1% v/v, and as a positive control, an extract from *Eucalyptus globulus* prepared as shown below was added to be the final concentration shown in Table 7. An effect of enhancing production of ceramide is known for the extract from *Eucalyptus globulus*, and the extract was used as the positive control.

The cells were cultured for 3 days, and then the respective cells were collected from each well.

An organic phase, contained lipids extracted from the collected cells by the Blight and Dyer method, was transferred into a glass tube, and was dried to solid in nitrogen stream. Subsequently, the dried product was redissolved in chloroform and methanol, and this was used as a lipid sample.

Further, 0.1 N NaOH and a 1% aqueous SDS solution were added to the cells from which lipids had been extracted, and the mixture was heated at 60° C. for 2 hours to thereby solubilize proteins. The mixture was cooled to room temperature, and then 2N HCl was added for neutralization. The amount of proteins was quantified by the BCA method.

The lipid sample thus prepared was developed two times in a horizontal position by thin layer chromatography (TLC) using chloroform:methanol:acetic acid=190:9:1. A copper sulfate solution was sprayed, followed by baking on a hot plate, to thereby detect ceramides. This was designated as the ceramide amount. Herein, the ceramide amount represents the relative value in the case where the ceramide amount was designated as 1 when the 50 vol % ethanol was added.

The results are shown in Table 7.

Reference Example 40 g of the leaves of *Eucalyptus globulus Labillardiere* (available from SHINWA BUSSAN CO., LTD.) finely was cut, and 400 mL of 50 vol % ethanol was added thereto. Then, extraction was carried out for 7 days under the conditions of standing at room temperature. Thereafter, the extract was filtered to obtain 291 mL of an extract from *Eucalyptus globulus Labillardiere*. For the extract thus obtained, the evaporation residue was calculated, and the evaporation residue was found to be 3.16% (w/v). This residue was diluted with a 50 vol % ethanol aqueous solution to prepare a 1.0% (w/v) extract.

TABLE 7

| Sample | Final concentration of extract (Concentration of extract of solid content 1%: v/v) | Ceramide amount |
|---|---|---|
| Control (50 vol % ethanol) | — | 1.00 ± 0.73 (n = 3) |
| Positive control (Extract from *Eucalyptus globulus Labillardiere*) | 0.001% | 1.21 (n = 2) |

TABLE 7-continued

| Sample | Final concentration of extract (Concentration of extract of solid content 1%: v/v) | Ceramide amount |
|---|---|---|
| Preparation Example 1-2 | 0.1% | 2.26 ± 0.77 (n = 3) |
|  | 0.05% | 3.62 ± 1.30 (n = 3) |
|  | 0.01% | 2.30 ± 1.02 (n = 3) |
| Preparation Example 2-2 | 0.01% | 1.25 (n = 2) |

As shown in Table 7, in the systems to which an extract from *Justicia procumbens* or *Peristrophe japonica* was added, an increase in the amount of ceramide production was recognized as compared to the control system. Thus, it was understood that the ceramide production enhancer of the present invention containing the extract from *Justicia procumbens* or *Peristrophe japonica* as an active ingredient, can enhance ceramide production.

Further, the ceramide is related to maintenance of a skin barrier function, maintenance or improvement of a moisturizing function, and prevention or improvement of skin roughness. Thus, prevention of epidermal incomplete cornification, improvement of the skin moisturizing function, and prevention or improvement of the skin roughness or the like can be attained by enhancing the ceramide production. Accordingly, an extract from *Justicia procumbens* and/or an extract from *Peristrophe japonica* having the ceramide production enhancing effect can be contained as the active ingredient in the epidermal cornification improver, the skin moisturizing function improver, the skin barrier function improver, and the skin roughness preventive or improver.

Test Example 2-2 Verification of Ceramide Production Enhancing Effect

Normal human epidermal keratinocytes (trade name: NHEK(F), manufactured by Kurabo Industries, Ltd.) were cultured under the conditions of 37° C. and 5% $CO_2$, in a culture medium (trade name: EpiLife-KG2, manufactured by Kurabo Industries, Ltd.) using a culture plate.

Thereafter, the culture medium was exchanged with EpiLife-KG2 without growth factors such as epidermal growth factor, and the exemplified compound (12) was added to the culture fluid in an amount of 0.1 μM. In place of the exemplified compound (12), as a control, the 50 vol % ethanol was added in the final concentration of 0.01%.

The cells were cultured for 3 days, and then the respective cells were collected from each well.

A ceramide amount was measured using recovered cells in a manner similar to Test Example 2-1. Herein, the ceramide amount represents the relative value in the case where the ceramide amount was designated as 1 when the 50 vol % ethanol was added.

The results are shown in Table 8.

TABLE 8

| Sample | Final concentration of extract | Ceramide amount (Average value in n = 2) |
|---|---|---|
| Control (50 vol % ethanol) | — | 1.00 |
| Exemplified compound (12) | 0.1 μM | 1.30 |

As shown in Table 8, in the system to which a compound represented by Formula (1) was added, an increase in the amount of ceramide production was recognized as compared to the control system. Thus, it was understood that the ceramide production enhancer of the present invention containing the compound represented by Formula (1) as an active ingredient, can enhance ceramide production.

Further, in a manner similar to the extract from *Justicia procumbens* and the extract from *Peristrophe japonica*, the compound represented by Formula (1) and having the ceramide production enhancing effect can be contained as the active ingredient in an epidermal cornification improver, a skin moisturizing function improver, a skin barrier function improver and a skin roughness preventive or improver.

Test Example 3-1 Evaluation of Involucrin Expression Amount (1) Cell Culture

Human epidermal keratinocyte line HaCaT was cultured in a culture medium in which 10% fetal calf serum inactivated, and 1% penicillin-streptomycin (manufactured by Gibco Laboratories) were added to DMEM (manufactured by Gibco Laboratories), under conditions of 37° C. and 5% $CO_2$.

(2) Evaluation of IVL Expression

In first screening, Involucrin ELISA Assay Kit BT-650 (trade name, manufactured by BTI) was used by modifying part of protocol. A detailed protocol is presented below.

In a 24-well plate, HaCaT cells were seeded in an amount of $5 \times 10^4$ pieces/well, and cultured. On the following day, exchange was carried out for a culture medium containing at a final concentration shown in Table 9 the extract from *Peristrophe japonica* prepared in Preparation Example 2-2 and to be 1.0% (w/v) in terms of a solid content, and culture was further carried out for 24 hours. In place of the extract from *Peristrophe japonica*, as a control, exchange was carried out for a culture medium containing at a final concentration of 0.5% v/v 50 vol % ethanol being an extraction solvent, and culture was further carried out for 24 hours, and thus the resultant cultured product was used. After 24 hours from addition of the extract, the cells were washed twice using PBS(–), and 400 μL of extraction buffer solution containing Complete Mini Protease Inhibitor Cocktail (trade name, manufactured by Roche) in 20 mM Tris-HCl (pH: 7.5)–2 mM EDTA was added to the cells. Herein, one particle of Protease Inhibitor Cocktail was added per 10 mL of extraction buffer solution. In the presence of this extraction buffer solution, the cells were exfoliated and collected by means of a cell scraper, and then subjected to ultrasonication by a sonicator. A supernatant collected by centrifuging this solution was used as a lysate for evaluation.

A total protein concentration of the lysate was quantitatively determined using BCA Protein Assay Kit (trade name, manufactured by Thermo Scientific, Inc.) according to manufacturer's instructions for use. The lysate was diluted with buffer B (2 mM EDTA, 5 g/L Tween 20, 2.5 g/L Gelatin in PBS) to be a total protein amount of 3 μg per well of a 96-well plate, and added to the 96-well plate. Then an anti-IVL antibody (a kit attachment, a dilution ratio: 1/300) was added thereto to allow a primary antibody response at 4° C. overnight. Moreover, to another 96-well plate (469078, manufactured by Nalge Nunc Corporation), a human IVL protein (kit attachment) was added by 1 ng/well for each, and an antigen was adsorbed at 4° C. overnight together with 10 μL/well of EDC (1-ethyl-3-(3-dimethylaminopropyl)carbodiimide, manufactured by Kanto Chemical Co., Inc.) as a condensing agent. On the following day, a solution in the plate on which the antigen was adsorbed was sucked and removed, and 100 μL of 0.1 M $NH_4Cl$ was added thereto to allow reaction at room temperature for 30 minutes. After the reaction, the resultant reaction product was washed 4 times with distilled $H_2O$ (manufactured by Gibco Laboratories), and once with buffer B, and then 100 μL of a primary antibody response liquid on the previous day was added thereto to allow reaction at room temperature for 30 minutes. After this reaction, the resultant reaction product was washed 5 times with buffer B, and an anti-rabbit AP Conjugate antibody (dilution ratio: 1/2,000) attached to the kit was added thereto to allow reaction at room temperature for 1 hour. After the reaction, the resultant reaction product was washed 4 times with buffer B, and once with buffer D (1 mM $MgCl_2.6H_2O$ in 0.05 M carbonate/bicarbonate (trade name: C3041-50CAP, manufactured by Sigma-Aldrich Corporation)), and then 100 μL of β-nitrophenylphosphate (1 mg/mL in buffer D, manufactured by Sigma-Aldrich Corporation) solution was added to allow a coloring reaction. After coloring was confirmed, absorbance at 405 nm was measured to quantitatively determine an IVL amount.

The results of evaluation are shown in Table 9. The IVL amount in the extract sample was expressed in terms of a relative value when the IVL amount of the control to which 50% ethanol was added was taken as 1.

TABLE 9

| Sample | Final concentration of extract (Concentration of extract of solid content 1%: v/v) | IVL amount (Average value in n = 2) |
|---|---|---|
| Control (50 vol % ethanol) | — | 1.00 |
| Preparation Example 2-2 | 0.5% | 1.30 |

As shown in Table 9, the involucrin expression amount increased in the system to which the extract from *Peristrophe japonica* was added.

Test Example 3-2 Evaluation of Involucrin Expression Amount (1) Cell Culture

Human epidermal keratinocyte line HaCaT was cultured in a culture medium in which 10% fetal calf serum inactivated, and 1% penicillin-streptomycin (manufactured by Gibco Laboratories) were added to DMEM (manufactured by Gibco Laboratories), under conditions of 37° C. and 5% $CO_2$.

(2) Evaluation of IVL Expression

In first screening, Involucrin ELISA Assay Kit BT-650 (trade name, manufactured by BTI) was used by modifying part of protocol. A detailed protocol is presented below.

In a 6-well plate, HaCaT cells were seeded in an amount of $5 \times 10^4$ pieces/well, and cultured. On the following day, exchange was carried out for a culture medium containing the exemplified compound (18) at a final concentration shown in Table 10, and culture was further carried out for 24 hours. In place of the exemplified compound (18), as a control, exchange was carried out for a culture medium containing at a final concentration of 0.1% v/v DMSO being a solvent, and culture was further carried out for 24 hours, and thus the resultant cultured product was used. After 24 hours from addition of the exemplified compound (18), the cells were washed twice using PBS(−), and total RNA was extracted using RNeasy (registered trademark) Mini Kit (manufactured by QIAGEN). A concentration of total RNA was measured, and a fixed amount of total RNA was used as a template, and a reverse transcription reaction was carried out using High capacity RNA-to-cDNA Kit (trade name, manufactured by Applied Biosystems, Inc.).

IVL gene expression was quantitatively determined from the resultant cDNA by Real-time RT-PCR. The gene expression was conducted in a 20 μL reaction system under amplification conditions in denaturation at 95° C. for 15 seconds, annealing at 60° C. for 1 minute, and an extension reaction. Each gene expression amount was corrected by a RPLPO expression amount, and expressed in terms of a relative value when an IVL gene expression amount upon addition of DMSO was taken as 1.

The results are shown in Table 10.

TABLE 10

| Sample | Final concentration of extract | IVL gene amount (Average value in n = 2) |
|---|---|---|
| Control (DMSO) | — | 1.00 |
| Exemplified compound (18) | 0.01 μM | 1.32 |

As shown in Table 10, the involucrin expression amount increased in the system to which the compound represented by Formula (1) was added.

Further, the involucrin expression is related to maintenance of a skin barrier function, maintenance or improvement of a moisturizing function, and prevention or improvement of skin roughness. Thus, prevention of epidermal incomplete cornification, improvement of the skin moisturizing function, and prevention or improvement of the skin roughness or the like can be attained by enhancing the involucrin expression. Moreover, a substance that increases the involucrin gene expression amount can be a wavy hair or frizzled hair enhancer, or a wave formation enhancer. Accordingly, at least one kind selected from the group consisting of an extract from *Peristrophe japonica* and a compound represented by Formula (1) having the involucrin expression enhancing effect can be contained as the active ingredient in the epidermal cornification improver, the skin moisturizing function improver, the skin barrier function improver, the skin roughness preventive or improver, and the wavy hair former.

Test Example 4

About 5 g of *Peristrophe japonica* (Lot. SB-3436) obtained from SHINWA BUSSAN KAISHA LTD. was immersed into lukewarm water, and a specialist identified the plant by microscopy. As a result, the plant was confirmed to contain a spike, and have a thin sepal and transparent white edging with existence of a long bristle. From these features, the plant obtained as Lot. SB-3436 was identified to be *Justicia procumbens* and not *Peristrophe japonica*.

Then, 600 g of *Justicia procumbens* obtained as Lot. SB-3436 was finely cut, 6,000 mL of 99.5 vol % ethanol aqueous solution was added thereto, and the resultant mixture was subjected to extraction under conditions of room temperature and still standing for 7 days. Then, the resultant extract was filtered to obtain 4,504 mL of an extract from *Justicia procumbens*. To 4,000 mL of the resultant extract, 2,000 mL of hexane was added, and the resultant mixture was stirred, and then 6,000 mL of water was further added thereto. After the resultant mixture was subjected to liquid-liquid distribution, and then 8,367 mL of lower layer was taken out. To 2,500 mL of the resultant extract, 1,000 mL of 1,3-butylene glycol was added, and the resultant mixture was concentrated by an evaporator to remove ethanol and water. Thereto, 1,500 mL of water was added, and then subjected to sedimentation under conditions of 5° C. and 4 days. An insoluble matter was removed by filtration, and then a 40 vol % 1,3-butylene glycol aqueous solution was to 2,403 L of the resultant filtrate to prepare 3,266 mL of extract. When a residue on evaporation was calculated on the resultant extract, the residue on evaporation was 0.02% (w/v).

To each of right-left cheek portions and outsides of lower legs of 10 healthy men and women, skin lotions formulated each with the extract from *Justicia procumbens* and having a composition shown in Table 11, or placebo skin lotions were continuously applied for 4 weeks twice a day. After the skin lotions were applied for 4 weeks, application of these skin lotions was discontinued.

TABLE 11

| Compositioning components | Placebo skin lotion | Skin lotion compositioning extract from *Justicia procumbens* |
|---|---|---|
| Extract from *Justicia procumbens* | — | 10 mass % |
| 1,3-Butylene glycol | 5 mass % | 1 mass % |
| Ethanol | 10 mass % | 10 mass % |
| Ion exchanged water | 85 mass % | 79 mass % |
| Total % | 100 mass % | 100 mass % |

Horny cell layer moisture contents and skin surface roughness in each of the cheek portions and the outsides of the lower legs before starting application of the skin lotion (0W), after continuous application of the skin lotion for 4 weeks (4W), and after 1 week from discontinuation of application of the skin lotion (5W) were measured by the following methods to evaluate skin properties.

(Measurement of Horny Cell Layer Moisture Content)

On the day of measurement, a region to be measured was cleaned, and then conditioned under an environment set at 20° C. and 40% of humidity.

Corneometer CM825MP (trade name, manufactured by Courage+Khazaka Electronic GmbH) was used to measure capacitance 5 times per one region, and a mean value in measurement 5 times was taken as a capacitance value of the above-described measured region for each subject to evaluate the horny cell layer moisture content. The results are shown in Table 12 (cheek portions) and Table 13 (outsides of lower legs). In addition, a mean value of 10 subjects for amounts of change of capacitance values after continuous application of the skin lotion for 4 weeks (4W), and after 1 week from discontinuation of application of the skin lotion (5W) when the capacitance value before application of the skin lotion was taken as 1 was taken as Δ(capacitance value) in the region.

Measurement of Skin Surface Roughness

On the day of measurement, a region to be measured was cleaned, and then conditioned under an environment set at 20° C. and 40% of humidity.

Visioscan VC98 (trade name, manufactured by Courage+Khazaka Electronic GmbH) was used to pick up two images per one region and to calculate an SELS parameter (SEr) per fixed area using attached analysis software, and a mean value of the two images was taken as an SEr value of the above-described measured region for each subject to evaluate the skin surface roughness. The results are shown in Table 14 (cheek portions) and Table 15 (outsides of lower legs). In addition, a mean value of 10 subjects for amounts of change of the SELS parameters after continuous application of the skin lotion for 4 weeks (4W), and after 1 week from discontinuation of application of the skin lotion (5W) when the SELS parameter before application of the skin lotion was taken as 0 was taken as ΔSEr in the region.

TABLE 12

(n = 10)
Horny cell layer moisture content at cheek portion (Δ(capacitance value), changed amount from 0 W)

| | 0 W | 4 W | 5 W |
|---|---|---|---|
| Placebo skin lotion | 0 | −0.67 ± 11.77 | 1.85 ± 7.70 |
| Skin lotion compositioning extract from *Justicia procumbens* | 0 | −1.08 ± 12.21 | 3.32 ± 8.26 |

TABLE 13

(n = 10)
Horny cell layer moisture content at outside of lower leg (Δ(capacitance value), changed amount from 0 W)

| | 0 W | 4 W | 5 W |
|---|---|---|---|
| Placebo skin lotion | 0 | −1.33 ± 4.76 | −1.54 ± 4.12 |
| Skin lotion compositioning extract from *Justicia procumbens* | 0 | −0.26 ± 4.65 | −0.87 ± 4.39 |

TABLE 14

(n = 10)
Skin surface roughness at cheek portion (ΔSEr, changed amount from 0 W)

| | 0 W | 4 W | 5 W |
|---|---|---|---|
| Placebo skin lotion | 0 | 0.01 ± 0.89 | 0.63 ± 1.36 |
| Skin lotion compositioning extract from *Justicia procumbens* | 0 | −0.32 ± 1.68 | −0.28 ± 1.53 p = 0.10 vs. placebo |

TABLE 15

(n = 10)
Skin surface roughness at outside of lower leg (ΔSEr, changed amount from 0 W)

| | 0 W | 4 W | 5 W |
|---|---|---|---|
| Placebo skin lotion | 0 | 1.17 ± 1.41 | 1.31 ± 1.80 |
| Skin lotion compositioning extract from *Justicia procumbens* | 0 | 0.42 ± 1.36 | −0.11 ± 1.34 p = 0.06 vs. placebo |

As shown in Table 12, in the cheek portion, an amount of change from an initial value (0W), represented by Δ(capacitance value), for the horny cell layer moisture content at 5W was larger in the portion to which the skin lotion formulated with the extract from *Justicia procumbens* was applied in comparison with the portion to which the placebo skin lotion was applied. More specifically, the results in Table 12 show that the extract from *Justicia procumbens* has an effect of increasing the horny cell layer moisture content.

As shown in Table 13, in the outside of the lower leg, from values of amounts of change from an initial value (0W) for the horny cell layer moisture contents at 4W and 5W, an amount of moisture reduction is found to be smaller in the portion to which the skin lotion formulated with the extract from *Justicia procumbens* was applied in comparison with the portion to which the placebo skin lotion was applied. More specifically, the results in Table 13 show that the extract from *Justicia procumbens* has an effect of inhibiting the horny cell layer moisture content reduction.

As shown in Table 14, in the cheek portion, from values of amounts of change from an initial value (0W), represented by ΔSEr, for the skin surface roughness at 4W and 5W, while the skin surface roughness is found increase in the portion to which the placebo skin lotion was applied, the skin surface roughness is found to decrease in the portion to which the skin lotion formulated with the extract from *Justicia procumbens* was applied. More specifically, the results in Table 14 show that the extract from *Justicia procumbens* has an effect of preventing or improving the skin roughness in the cheek portion.

As shown in Table 15, in the outside of the lower leg, from values of amounts of change from an initial value (0W), represented by ΔSEr, for the skin surface roughness at 4W and 5W, while the skin surface roughness is found increase in the portion to which the placebo skin lotion was applied, the skin surface roughness is found to decrease in the portion to which the skin lotion formulated with the extract from *Justicia procumbens* was applied. More specifically, the results in Table 15 show that the extract from *Justicia procumbens* has the effect of preventing or improving the skin roughness in the outside of the lower leg.

As described above, the extract from *Justicia procumbens* has the effect of increasing the horny cell layer moisture content, the effect of inhibiting the horny cell layer moisture content reduction, and the effect of preventing or improving the skin roughness. Accordingly, the extract from *Justicia procumbens* can be contained as the active ingredient in the epidermal cornification improver, the skin moisturizing function improver, the skin barrier function improver, the horny cell layer moisture content increasing agent, the horny cell layer moisture content reduction inhibitor, and the skin roughness preventive or improver.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2012-188767 filed in Japan on Aug. 29, 2012, Patent Application No. 2012-188768 filed in Japan on Aug. 29, 2012, and Patent Application No. 2012-278068 filed in Japan on Dec. 20, 2012, each of which is entirely herein incorporated by reference.

The invention claimed is:

1. A method of activating transglutaminase in skin epidermal keratinocytes of a human subject in need thereof, comprising externally applying, to the subject's skin epidermal keratinocytes, a composition that comprises an effective amount of at least one compound represented by Formula (1):

Formula (1)

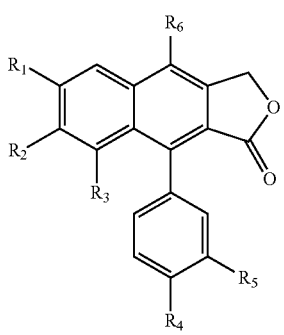

wherein the skin is dry skin as a result of atopic dermatitis, xerosis, or psoriasis, wherein $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid, and activating transglutaminase by increasing transglutaminase activity in the skin epidermal keratinocytes as a result of the applying.

2. The method according to claim 1, wherein the compound represented by Formula (1) is a compound represented by Formula (11), or a compound represented by any one of Formulas (2) to (4):

Formula (11)

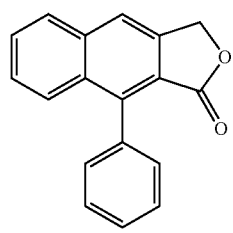

Formula (2)

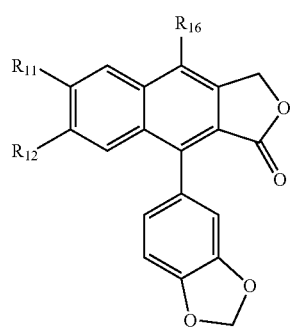

wherein, in Formula (2), $R_{11}$ and $R_{12}$ each independently represent a hydrogen atom, a hydroxyl group, or a linear or branched alkoxy group having 1 to 4 carbon atoms; $R_{16}$ represents a hydrogen atom, a hydroxyl group, a linear or branched alkoxy group having 1 to 5 carbon atoms, or a linear or branched acyloxy group having 1 to 4 carbon atoms;

Formula (3)

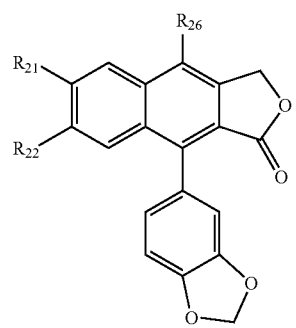

wherein, in Formula (3), $R_{21}$ and $R_{22}$ each independently represent a hydrogen atom, a hydroxyl group, or a linear or branched alkoxy group having 1 to 4 carbon atoms; $R_{26}$ represents a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid; and Formula (4)

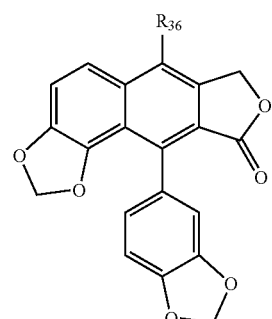

wherein, in Formula (4), $R_{36}$ represents a hydrogen atom, a hydroxyl group, linear or branched alkoxy group having 1 to 5 carbon atoms, or a linear or branched acyloxy group having 1 to 4 carbon atoms.

3. A method of improving epidermal cornification by activating transglutaminase in skin epidermal keratinocytes in a human subject in need thereof, comprising externally applying, to the subject's skin epidermal keratinocytes, a composition that comprises an effective amount of at least one compound represented by Formula (1):

Formula (1)

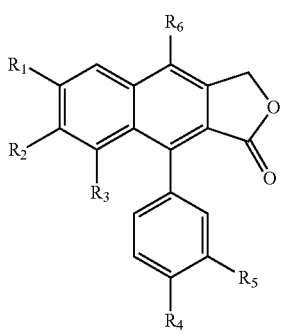

wherein the skin is dry skin as a result of atopic dermatitis, xerosis, or psoriasis, wherein $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid, and activating transglutaminase by increasing transglutaminase activity in the skin epidermal keratinocytes as a result of the applying.

4. The method according to claim 3, wherein the compound represented by Formula (1) is a compound represented by Formula (11), or a compound represented by any one of Formulas (2) to (4):

Formula (11)

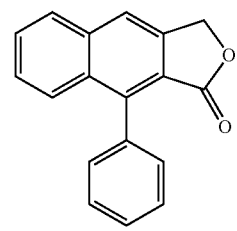

Formula (2)

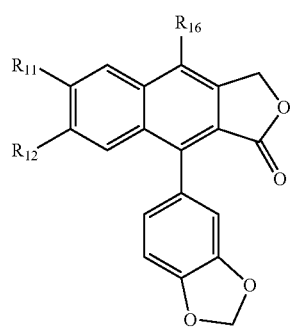

wherein, in Formula (2), $R_{11}$ and $R_{12}$ each independently represent a hydrogen atom, a hydroxyl group, or a linear or branched alkoxy group having 1 to 4 carbon atoms; $R_{16}$ represents a hydrogen atom, a hydroxyl group, a linear or branched alkoxy group having 1 to 5 carbon atoms, or a linear or branched acyloxy group having 1 to 4 carbon atoms;

Formula (3)

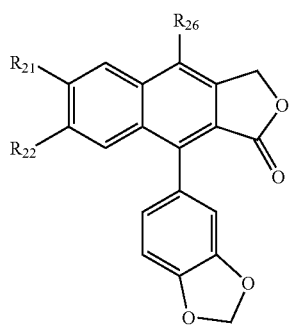

wherein, in Formula (3), $R_{21}$ and $R_{22}$ each independently represent a hydrogen atom, a hydroxyl group, or a linear or branched alkoxy group having 1 to 4 carbon atoms; $R_{26}$ represents a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid; and Formula (4)

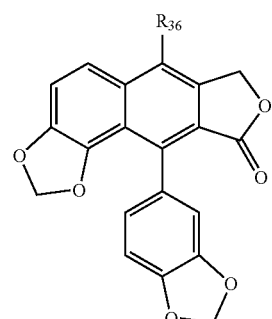

wherein, in Formula (4), $R_{36}$ represents a hydrogen atom, a hydroxyl group, a linear or branched alkoxy group having 1 to 5 carbon atoms, or a linear or branched acyloxy group having 1 to 4 carbon atoms.

5. A method of improving skin moisturizing by activating transglutaminase in skin epidermal keratinocytes, in a human subject in need thereof, comprising externally applying, to the subject's skin epidermal keratinocytes, a composition that comprises an effective amount of at least one compound represented by Formula (1):

Formula (1)

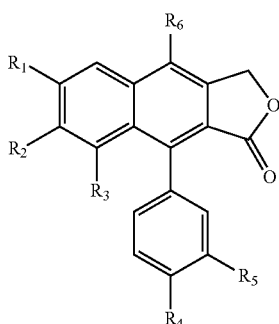

wherein the skin is dry skin as a result of atopic dermatitis, xerosis, or psoriasis, wherein $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid, and activating transglutaminase by increasing transglutaminase activity in the skin epidermal keratinocytes as a result of the applying.

6. The method according to claim 5, wherein the compound represented by Formula (1) is a compound represented by Formula (11), or a compound represented by any one of Formulas (2) to (4):

Formula (11)

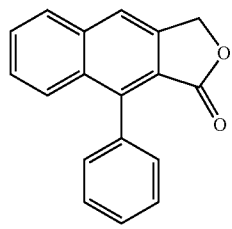

Formula (2)

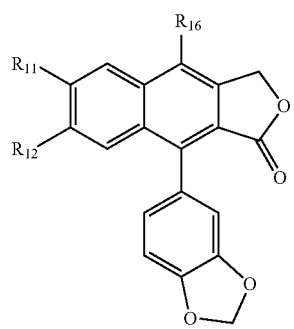

wherein, in Formula (2), $R_{11}$ and $R_{12}$ each independently represent a hydrogen atom, a hydroxyl group, or a linear or branched alkoxy group having 1 to 4 carbon atoms; $R_{16}$ represents a hydrogen atom, a hydroxyl group, a linear or branched alkoxy group having 1 to 5 carbon atoms, or a linear or branched acyloxy group having 1 to 4 carbon atoms;

Formula (3)

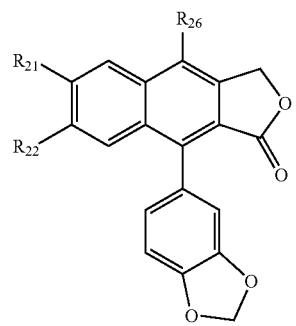

wherein, in Formula (3), $R_{21}$ and $R_{22}$ each independently represent a hydrogen atom, a hydroxyl group, or a linear or branched alkoxy group having 1 to 4 carbon atoms; $R_{26}$ represents a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid; and Formula (4)

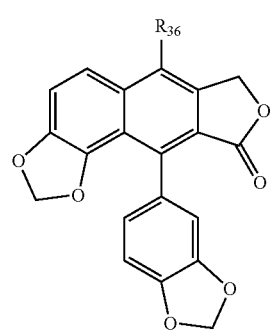

wherein, in Formula (4), $R_{36}$ represents a hydrogen atom, a hydroxyl group, a linear or branched alkoxy group having 1 to 5 carbon atoms, or a linear or branched acyloxy group having 1 to 4 carbon atoms.

7. A method of improving a skin barrier function by activating transglutaminase in skin epidermal keratinocytes in a human subject in need thereof, comprising externally applying, to the subject's skin epidermal keratinocytes, a composition that comprises an effective amount of at least one compound represented by Formula (1):

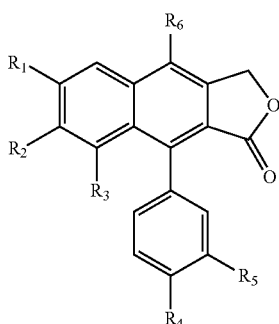

Formula (1)

wherein the skin is dry skin as a result of atopic dermatitis, xerosis, or psoriasis, wherein $R_1$ and $R_2$ each independently represent a hydrogen atom, a hydroxyl group, or a linear or branched alkoxy group having 1 to 4 carbon atoms; $R_3$ represents a hydrogen atom, or a group for fouling a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid, and activating transglutaminase by increasing transglutaminase activity in the skin epidermal keratinocytes as a result of the applying.

8. The method according to claim 7, wherein the compound represented by Formula (1) is a compound represented by Formula (11), or a compound represented by any one of Formulas (2) to (4):

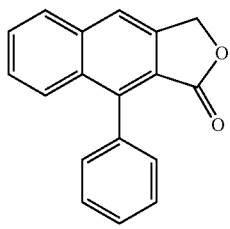

Formula (11)

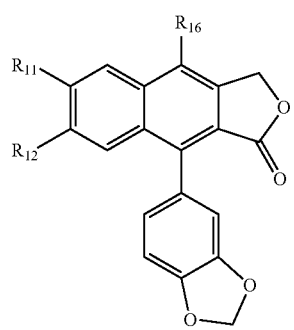

Formula (2)

wherein, in Formula (2), $R_{11}$ and $R_{12}$ each independently represent a hydrogen atom, a hydroxyl group, or a linear or branched alkoxy group having 1 to 4 carbon atoms; $R_{16}$ represents a hydrogen atom, a hydroxyl group, a linear or branched alkoxy group having 1 to 5 carbon atoms, or a linear or branched acyloxy group having 1 to 4 carbon atoms;

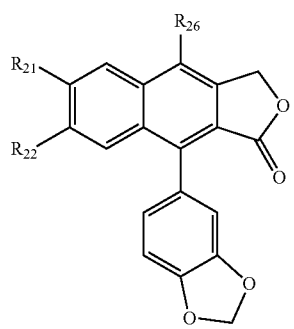

Formula (3)

wherein, in Formula (3), $R_{21}$ and $R_{22}$ each independently represent a hydrogen atom, a hydroxyl group, or a linear or branched alkoxy group having 1 to 4 carbon atoms; $R_{26}$ represents a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid; and

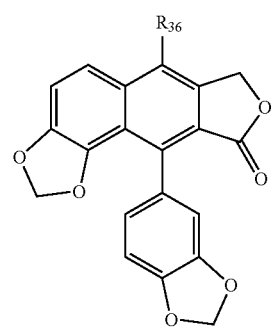

Formula (4)

wherein, in Formula (4), $R_{36}$ represents a hydrogen atom, a hydroxyl group, a linear or branched alkoxy group having 1 to 5 carbon atoms, or a linear or branched acyloxy group having 1 to 4 carbon atoms.

9. A method of increasing the moisture content of a horny cell layer in skin by activating transglutaminase in the skin's epidermal keratinocytes in a human subject in need thereof, comprising externally applying, to the subject's skin epidermal keratinocytes, a composition comprising an effective amount of at least one compound represented by Formula (1),

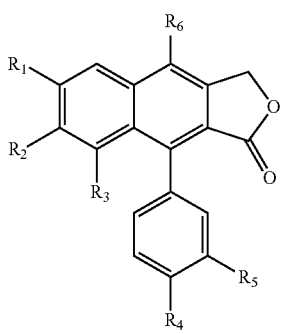

Formula (1)

wherein the skin is dry skin as a result of atopic dermatitis, xerosis, or psoriasis, wherein $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid, and activating transglutaminase by increasing transglutaminase activity in the skin epidermal keratinocytes as a result of the applying.

10. A method of inhibiting the reduction of moisture content in a horny cell layer in skin by activating transglutaminase in the skin's epidermal keratinocytes in a human subject in need thereof, comprising externally applying, to the subject's skin epidermal keratinocytes, a composition comprising an effective amount of at least one compound represented by Formula (1),

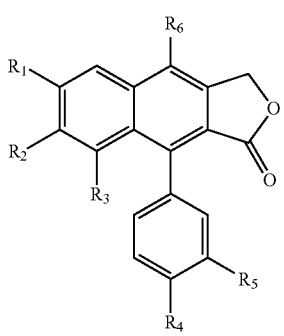

Formula (1)

wherein the skin is dry skin as a result of atopic dermatitis, xerosis, or psoriasis, wherein $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid, and activating transglutaminase by increasing transglutaminase activity in the skin epidermal keratinocytes as a result of the applying.

11. A method of preventing or improving skin roughness, by activating transglutaminase in the skin's epidermal keratinocytes in a human subject in need thereof, comprising externally applying, to the subject's skin epidermal keratinocytes, a composition comprising an effective amount of at least one compound represented by Formula (1):

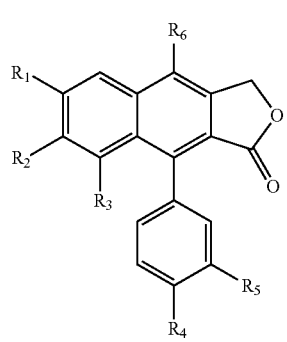

Formula (1)

wherein the skin is dry skin as a result of atopic dermatitis, xerosis, or psoriasis, wherein $R_1$ and $R_2$ each independently represent a hydrogen atom, a hydroxyl group, or a linear or branched alkoxy group having 1 to 4 carbon atoms; $R_3$ represents a hydrogen atom, or a group for forming a methylenedioxy group by bonding with $R_2$; $R_4$ and $R_5$ each represent a hydrogen atom, or a group for forming a methylenedioxy group by bonding with each other; $R_6$ represents a hydrogen atom, a hydroxyl group, a linear or branched alkoxy group having 1 to 5 carbon atoms, a linear or branched acyloxy group having 1 to 4 carbon atoms, or a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid, and activating transglutaminase by increasing transglutaminase activity in the skin epidermal keratinocytes as a result of the applying.

12. The method according to claim 11, wherein the compound represented by Formula (1) is a compound represented by Formula (11), or a compound represented by any one of Formulas (2) to (4):

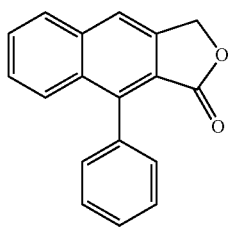

Formula (11)

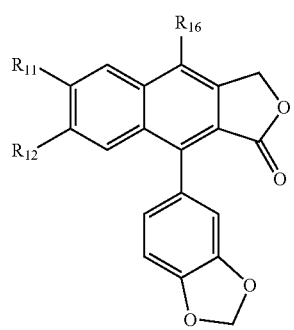

Formula (2)

wherein, in Formula (2), $R_{11}$ and $R_{12}$ each independently represent a hydrogen atom, a hydroxyl group, or a linear or branched alkoxy group having 1 to 4 carbon atoms; $R_{16}$ represents a hydrogen atom, a hydroxyl group, a linear or branched alkoxy group having 1 to 5 carbon atoms, or a linear or branched acyloxy group having 1 to 4 carbon atoms;

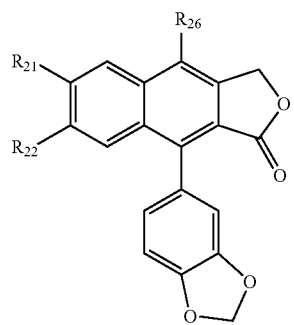

Formula (3)

wherein, in Formula (3), $R_{21}$ and $R_{22}$ each independently represent a hydrogen atom, a hydroxyl group, or a linear or branched alkoxy group having 1 to 4 carbon atoms; $R_{26}$ represents a sugar residue selected from the group consisting of (D-apio-β-D-furanosyl)oxy, (5-O-acetyl-D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; and the hydroxyl group in the sugar residue may form an ester with a carboxylic acid; and

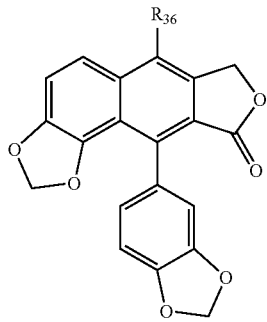

Formula (4)

wherein, in Formula (4), $R_{36}$ represents a hydrogen atom, a hydroxyl group, a linear or branched alkoxy group having 1 to 5 carbon atoms, or a linear or branched acyloxy group having 1 to 4 carbon atoms.

13. The method according to claim 3, wherein the compound is Justicidin B.

14. The method according to claim 5, wherein the compound is Justicidin B.

15. The method according to claim 7, wherein the compound is Justicidin B.

16. The method according to claim 11, wherein the compound is Justicidin B.

17. The method according to claim 1, wherein the compound is Justicidin B.

18. The method according to claim 1, wherein $1.0 \times 10^{-7}$ mg to 0.1 g of the compound is applied per day per 60 kg body weight.

19. The method according to claim 3, wherein $1.0 \times 10^{-7}$ mg to 0.1 g of the compound is applied per day per 60 kg body weight.

20. The method according to claim 5, wherein $1.0 \times 10^{-7}$ mg to 0.1 g of the compound is applied per day per 60 kg body weight.

21. The method according to claim 7, wherein $1.0 \times 10^{-7}$ mg to 0.1 g of the compound is applied per day per 60 kg body weight.

22. The method according to claim 11, wherein $1.0 \times 10^{-7}$ mg to 0.1 g of the compound is applied per day per 60 kg body weight.

* * * * *